US011441141B2

(12) United States Patent
Rummel

(10) Patent No.: US 11,441,141 B2
(45) Date of Patent: Sep. 13, 2022

(54) METHODS FOR THE MANUFACTURE OF PROTEOLYTICALLY PROCESSED POLYPEPTIDES

(71) Applicant: IPSEN BIOINNOVATION LIMITED, Abingdon (GB)

(72) Inventor: Andreas Rummel, Hannover (DE)

(73) Assignee: IPSEN BIOINNOVATION LIMITED, Abingdon (GB)

( * ) Notice: Subject to any disclaimer, the term of this patent is extended or adjusted under 35 U.S.C. 154(b) by 0 days.

(21) Appl. No.: 16/928,107

(22) Filed: Jul. 14, 2020

(65) Prior Publication Data

US 2020/0339971 A1 Oct. 29, 2020

Related U.S. Application Data

(63) Continuation of application No. 16/105,120, filed on Aug. 20, 2018, now Pat. No. 10,808,236, which is a continuation of application No. 14/423,222, filed as application No. PCT/EP2012/073283 on Nov. 21, 2012, now Pat. No. 10,087,432.

(51) Int. Cl.

| | |
|---|---|
| *C12N 9/52* | (2006.01) |
| *C07K 14/33* | (2006.01) |
| *C12N 9/50* | (2006.01) |
| *C12Q 1/37* | (2006.01) |

(52) U.S. Cl.

CPC ................ *C12N 9/52* (2013.01); *C07K 14/33* (2013.01); *C12N 9/50* (2013.01); *C12Q 1/37* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 5,846,929 | A | 12/1998 | Johnson et al. |
| 6,967,088 | B1 | 11/2005 | Williams et al. |
| 7,081,529 | B2 | 7/2006 | Smith et al. |
| 7,132,259 | B1 | 11/2006 | Dolly et al. |
| 7,172,764 | B2 | 2/2007 | Li et al. |
| 7,214,787 | B1 | 5/2007 | Smith et al. |
| 7,227,010 | B2 | 6/2007 | Smith |
| 7,419,676 | B2 | 9/2008 | Dolly et al. |
| 7,452,543 | B2 | 11/2008 | Chaddock et al. |
| 7,465,457 | B2 | 12/2008 | Johnson et al. |
| 7,514,088 | B2 | 4/2009 | Steward et al. |
| 7,556,817 | B2 | 7/2009 | Steward et al. |
| 7,659,092 | B2 | 2/2010 | Foster et al. |
| 7,727,538 | B2 | 6/2010 | Quinn et al. |
| 7,740,868 | B2 | 6/2010 | Steward et al. |
| 7,749,514 | B2 | 7/2010 | Steward et al. |
| 7,811,584 | B2 | 10/2010 | Steward et al. |
| 7,833,524 | B2 | 11/2010 | Johnson et al. |
| 7,892,565 | B2 | 2/2011 | Steward et al. |
| 7,897,157 | B2 | 3/2011 | Steward et al. |
| 7,959,933 | B2 | 6/2011 | Dolly et al. |
| 7,985,411 | B2 | 7/2011 | Dolly et al. |
| 7,993,656 | B2 | 8/2011 | Steward et al. |
| 7,998,489 | B2 | 8/2011 | Steward et al. |
| 8,021,859 | B2 | 9/2011 | Steward et al. |
| 8,052,979 | B2 | 11/2011 | Steward et al. |
| 8,067,200 | B2 | 11/2011 | Foster et al. |
| 8,124,074 | B2 | 2/2012 | Foster et al. |
| 8,124,405 | B2 | 2/2012 | Foster et al. |
| 8,153,397 | B2 | 4/2012 | Smith et al. |
| 8,198,034 | B2 | 6/2012 | Fernandez-Salas et al. |
| 8,236,513 | B2 | 8/2012 | Atassi |
| 8,273,358 | B2 | 9/2012 | Steward et al. |
| 8,293,230 | B2 | 10/2012 | Rummel |
| 8,361,789 | B2 | 1/2013 | Zhu et al. |
| 8,372,615 | B2 | 2/2013 | Foster et al. |
| 8,399,400 | B2 | 3/2013 | Foster et al. |
| 8,399,401 | B2 | 3/2013 | Foster et al. |
| 8,455,213 | B2 | 6/2013 | Zhu et al. |
| 8,455,247 | B2 | 6/2013 | Zhu et al. |
| 8,455,248 | B2 | 6/2013 | Zhu et al. |
| 8,476,024 | B2 | 7/2013 | Marhold et al. |
| 8,481,040 | B2 | 7/2013 | Rummel et al. |

(Continued)

FOREIGN PATENT DOCUMENTS

| | | | |
|---|---|---|---|
| EP | 2264052 | A2 | 12/2010 |
| EP | 2524963 | A1 | 11/2012 |

(Continued)

OTHER PUBLICATIONS

Deppe et al, Toxins, 2020, 12, 743. 22 pages. Published: Nov. 26, 2020 (Year: 2020).*
Yang et al, Abstracts/Toxicon, 2018, 156:S118, abstract No. 272 (Year: 2018).*
Supotnitskiy, M.V., Biopreparaty, 1:6-15 (2011) (Abstract).
Clemens et al., Plastic and Reconstructive Surgery, 123:64-70 (2009).
Eleopra et al., Neurotox. Res., 9:127-131 (2006).
Estey et al., J. Ph arm Sci., 98:2994-3012 (2009).
Giminez et al., Toxicon, 32:1137-1146 (1994) □.
Hallis et al., J. Clin. Microbial., 34:1934-1938 (1996).
Mikolajczk et al., J. Biol. Chem., 278:10458-10464 (2003).
Prabakaran et al., Toxicon, 39:1515-1531 (2001).
Raijmakers et al., Chem. Commun., 46:8827-8829 (2010).
(Continued)

*Primary Examiner* — Nita M. Minnifield
(74) *Attorney, Agent, or Firm* — Gene J. Yao; Barnes & Thornburg LLP

(57) ABSTRACT

A proteolytically active polypeptide comprising an acid sequence having at least 50% sequence identity with the sequence of SEQ ID NO: 1 with the proviso that the polypeptide does not comprise the amino acid sequence of SEQ ID NO: 1. A nucleic acid encoding the polypeptide. An antibody specifically binding to the polypeptide. A method for the manufacture of a proteolytically processed polypeptide comprising contacting a first polypeptide having at least 50% sequence identity to SEQ ID NO: 1 with a second polypeptide that is susceptible to proteolysis by said first polypeptide.

20 Claims, 17 Drawing Sheets

Specification includes a Sequence Listing.

(56) References Cited

U.S. PATENT DOCUMENTS

| | | | |
|---|---|---|---|
| 8,486,422 B2 * | 7/2013 | Verhagen | C07K 14/33 424/239.1 |
| 8,492,109 B2 | 7/2013 | Oyler et al. | |
| 8,883,172 B2 | 11/2014 | Shone et al. | |
| 8,940,870 B2 | 1/2015 | Foster et al. | |
| 8,956,847 B2 | 2/2015 | Foster et al. | |
| 9,072,736 B2 | 7/2015 | Foster et al. | |
| 9,115,350 B2 | 8/2015 | Rummel et al. | |
| 9,193,771 B2 | 11/2015 | Hofmann et al. | |
| 9,234,011 B2 | 1/2016 | Rummel | |
| 9,243,301 B2 | 1/2016 | Foster et al. | |
| 9,340,813 B2 | 5/2016 | Ghanshani et al. | |
| 9,370,548 B2 | 6/2016 | Brin et al. | |
| 9,422,344 B2 | 8/2016 | Rummel | |
| 9,447,175 B2 | 9/2016 | Pfeil et al. | |
| 9,511,114 B2 | 12/2016 | Hofmann et al. | |
| 9,650,622 B2 | 5/2017 | Rummel et al. | |
| 9,808,540 B2 | 11/2017 | Lee et al. | |
| 9,827,298 B2 | 11/2017 | Hofmann et al. | |
| 9,938,514 B2 | 4/2018 | Ghanshani et al. | |
| 10,081,803 B2 | 9/2018 | Chaddock et al. | |
| 10,087,432 B2 * | 10/2018 | Rummel | A61P 1/06 |
| 10,266,816 B2 * | 4/2019 | Rummel | A61P 19/00 |
| 10,307,468 B2 * | 6/2019 | Palan | A61P 3/04 |
| 10,648,045 B2 | 5/2020 | Kwan et al. | |
| 10,704,038 B2 | 7/2020 | Chaddock et al. | |
| 10,808,236 B2 * | 10/2020 | Rummel | C12N 9/52 |
| 10,844,362 B2 * | 11/2020 | Dong | A61P 25/08 |
| 10,883,096 B2 * | 1/2021 | Rummel | A61P 17/02 |
| 11,007,245 B2 * | 5/2021 | Farrow | C07B 59/008 |
| 2003/0029912 A1 | 2/2003 | Li et al. | |
| 2004/0013687 A1 | 1/2004 | Simpson et al. | |
| 2004/0018589 A1 | 1/2004 | Zhong | |
| 2005/0106182 A1 | 5/2005 | Li et al. | |
| 2005/0169942 A1 | 8/2005 | Li et al. | |
| 2006/0211619 A1 | 9/2006 | Steward et al. | |
| 2006/0233836 A1 | 10/2006 | Kincaid et al. | |
| 2007/0166332 A1 | 7/2007 | Steward et al. | |
| 2008/0032930 A1 | 2/2008 | Steward et al. | |
| 2008/0032931 A1 | 2/2008 | Steward et al. | |
| 2008/0057575 A1 | 3/2008 | Fernandez-Salas et al. | |
| 2008/0096248 A1 | 4/2008 | Steward et al. | |
| 2008/0161226 A1 | 7/2008 | Steward et al. | |
| 2009/0004224 A1 | 1/2009 | Steward et al. | |
| 2009/0005313 A1 | 1/2009 | Steward et al. | |
| 2009/0018081 A1 | 1/2009 | Steward et al. | |
| 2009/0035822 A1 | 2/2009 | Foster et al. | |
| 2009/0069238 A1 | 3/2009 | Steward et al. | |
| 2009/0104234 A1 | 4/2009 | Francis et al. | |
| 2009/0114157 A1 | 5/2009 | Lee et al. | |
| 2010/0022751 A1 | 1/2010 | Shone et al. | |
| 2010/0041098 A1 | 2/2010 | Steward et al. | |
| 2010/0286371 A1 * | 11/2010 | Verhagen | C07K 14/33 530/350 |
| 2011/0086018 A1 | 4/2011 | Qian | |
| 2012/0107362 A1 | 5/2012 | Hofmann et al. | |
| 2012/0207734 A1 | 8/2012 | Jacky et al. | |
| 2012/0295330 A1 | 11/2012 | Ghanshani et al. | |
| 2012/0322092 A1 | 12/2012 | Tucker et al. | |
| 2013/0245227 A1 * | 9/2013 | Verhagen | C12N 9/52 530/350 |
| 2013/0281666 A1 | 10/2013 | Verhagen et al. | |
| 2013/0288336 A1 | 10/2013 | Verhagen et al. | |
| 2013/0315888 A1 | 11/2013 | Rummel et al. | |
| 2014/0030759 A1 | 1/2014 | Ghanshani et al. | |
| 2014/0045760 A1 | 2/2014 | Hofmann et al. | |
| 2014/0134643 A1 | 5/2014 | Pfeil et al. | |
| 2014/0308267 A1 | 10/2014 | Schmidt et al. | |
| 2015/0030584 A1 | 1/2015 | Rummel | |
| 2015/0038401 A1 | 2/2015 | Rummel et al. | |
| 2015/0044709 A1 * | 2/2015 | Eisele | C12N 9/0071 435/8 |
| 2015/0225709 A1 | 8/2015 | Rummel | |
| 2015/0232828 A1 | 8/2015 | Frevert et al. | |
| 2015/0232905 A1 | 8/2015 | Verhagen et al. | |
| 2016/0159866 A1 | 6/2016 | Ichtchenko et al. | |
| 2016/0319265 A1 | 11/2016 | Ghanshani et al. | |
| 2016/0030511 A1 | 12/2016 | Hofmann et al. | |
| 2017/0072030 A1 | 3/2017 | Hofmann et al. | |
| 2018/0117128 A1 | 5/2018 | Palan et al. | |
| 2019/0062721 A1 | 2/2019 | Chaddock et al. | |
| 2019/0100739 A1 * | 4/2019 | Rummel | C12N 9/50 |
| 2019/0127427 A1 | 5/2019 | Liu | |
| 2019/0153037 A1 | 5/2019 | Tucker et al. | |
| 2019/0153418 A1 | 5/2019 | Dong et al. | |
| 2019/0201505 A1 * | 7/2019 | Palan | A61P 3/04 |
| 2020/0024588 A1 | 1/2020 | Rummel et al. | |
| 2020/0224185 A9 | 7/2020 | Dong et al. | |
| 2020/0339971 A1 * | 10/2020 | Rummel | C07K 14/33 |

FOREIGN PATENT DOCUMENTS

| | | | | |
|---|---|---|---|---|
| WO | 00/33863 | 6/2000 | | |
| WO | 2002015700 | 2/2002 | | |
| WO | 2006059113 | 6/2006 | | |
| WO | 2007138339 | 12/2007 | | |
| WO | 2008008803 | 1/2008 | | |
| WO | 2008032931 | 3/2008 | | |
| WO | 2009/014854 | 1/2009 | | |
| WO | 2009015854 | 2/2009 | | |
| WO | 2010124998 | 11/2010 | | |
| WO | 2010138382 | 12/2010 | | |
| WO | 2010138387 | 12/2010 | | |
| WO | 2011091370 | 7/2011 | | |
| WO | 2012107362 | 8/2012 | | |
| WO | 2012112432 | 8/2012 | | |
| WO | 2014079495 | 5/2014 | | |
| WO | 2014080206 | 5/2014 | | |
| WO | WO-2014079497 A1 * | 5/2014 | | C07D 233/94 |
| WO | 2015166242 | 11/2015 | | |
| WO | 2016156113 | 10/2016 | | |

OTHER PUBLICATIONS

Shim et al., Blood, 104:415-419 (2004).
Smith et al., PLoS One, 2:e1271 (2007).
Kozaki et al., FEMS Microbiology Letters, 27: 149-154 (1985).
Gimenez et al., Biochimie, 72:213-217 (1990).
Kim et al., J. Chromatography B, 878:1973-1981 (2010).
Sigma Aldrich, "Endoproteinase Lys-C from Lysobacter enzymogenes suitable for Protein Sequencing product Information", Sigma-Aldrich, (20140000).
"Endoproteinase Lys-C Product information", Roche, (20110300), XP055463912.
Satorius et al., Toxicon, 51: 20 (2008).
Jensen et al., Toxicon, 41 :691-701 (2003).
Gadgil et al., Analytical Biochemistry, 355:165-174 (2006).
Lacy et al., J. Mol. Biol., 291: 1091-1104 (1999).
Ichtchenko et al., Neurotox Res., 9:234 (2006).
Krieglstein et al., J. Protein Chemistry, 13:49-57 (1994).
Markert et al., Protein Engineering, 16:1041-1046 (2013).
Briand et al., FESS Letters, 442:4347 (1999).
"Lysostaphin/LysKgene fusion, LysK-Lyso SEQ ID No:5.", Geneseq, (Apr. 15, 2010), Database accession No. AXV57358.
"Clostridium botulin urn toxin A di-chain loop region, SEQ ID No. 26.", Geneseq, (Mar. 31, 2011), Database accession No. AZF15196.
"Sequence 5 from patent U.S. Pat. No. 7,172,764.", Database accession No. ABN37706.
Agarwal et al., Biochemistry, 44: 11758-11765 (2005).
Fassio et al, Neuroscience, 90:893-902. (1999).
Schmidt et al, Biochemistry, 44:4067-4073 (2005).
Brown et al., Hybridoma, 16:447-457 (1997).
"Putative secreted protease; Thermolysin metallopeptidase; EC=3. 4.24—; Flags: Precursor;", Jun. 26, 2007, Database UniProt [Online], XP002690031, database accession No. A511 S4, http://ibis.internal.epo.org/exam/dbfetch.jsp?id=UNIPROT:A511S4.
M. Sebaihia, et al., "Genome sequence of proteolytic (Group I) Clostridium botulinum strain Hall A and comparative analysis of the clostridial genomes" Genome Research , Cold Spring Harbor Laboratory Press, Jul. 1, 2007, vol. 17 (7): 1082-1092, XP002530481, Woodbury, NY, US.

(56) References Cited

OTHER PUBLICATIONS

"Thermolysin metallopeptidase; EC=3.4.24—;", Sep. 11, 2007, Database UniProt [Online], XP002690032, database accession No. A7FTW9, http://ibis.internal.epo.org/exam/dbfetch.jsp?id=UNIPROT:A7FTW9.
Krieglstein et al., Eur. J. Biochem., 188: 39-45 (1990).
Krieglstein et al., Eur. J. Biochem., 202: 41-51 (1991).
Kozaki et al., Infection and Immunity, 10:750-756 (1974).
Shone et al., Eur. J. Biochem., 151: 75-82 (1985).
Dekleva et al., Journal of Bacteriology, 172: 2498-2503 (1990).
Mitchell et al., The Journal of Biological Chemistry, 243: 4683-4692 (1968).
Nilsson, et al., Annu Rev Biophys Biomol Struct., 34: 91-118 (2005).
Sugimura et al., Journal of Bacteriology, 170: 5625-5632 (1988).
Nonaka et al., The Journal of Biological Chemistry, 272: 30032-30039 (1997).
Hori et al., Acta Crystallographica Biilogical Crystallography, 057: 361-368 (2001).
Habermann et al., Journal of Neurochemistry, 51: 522-527 (1988).
Sathyamoorthy et al., The Journal of Biological Chemistry, 260: 10461-10466 (1985).
Rummel, et al., Molecular Microbiology 51: 631-643 (2004).
Wang et al., Analytical Chemistry, 84:4652-4658 (2012).
Dasgupta, J. Physiol., 84:220-228 (1990).
Japanese Office Action (with English translation) dated Apr. 6, 2016, for corresponding application No. JP 2015-535999.
Dasgupta et al., Biochemical Biophysical Research Communications, 48: 108-112, (1972).
Dasgupta et al., Toxicon, 22: 415-424 (1984).
Dekleva et al., Biochemical Biophysical Research Communication, 162: 767-772 (1989).
Eisele et al., Toxicon, 57: 555-565 (2011).
Galfre et al., Methods in Enzymology, 73: 3-46 (1981).
Jost et al., Drugs, 67: 669-683 (2007).
Kohler et al., Nature 256: 495-497 (1975).
Krieglstein et al., Journal Protein Chemistry, 13:49-57 (1994).
Lacy et al., Nature Structure Biology, 5: 898-902 (1998).
Malmborg et al., Journal Immunological Methods, 183:7-13 (1995).
Nonaka et al., Journal of Biochemistry, 124: 157-162 (1998).
Pearce et al., Toxicology and Applied Pharmacology, 128: 69-77 (1994).
Schier et al., Hum Antibodies Hybridomas, 7(3): 97-105 (1996).
Wright et al., Biochimica Biophysica Acta, 1443: 369-74 (1998).

\* cited by examiner

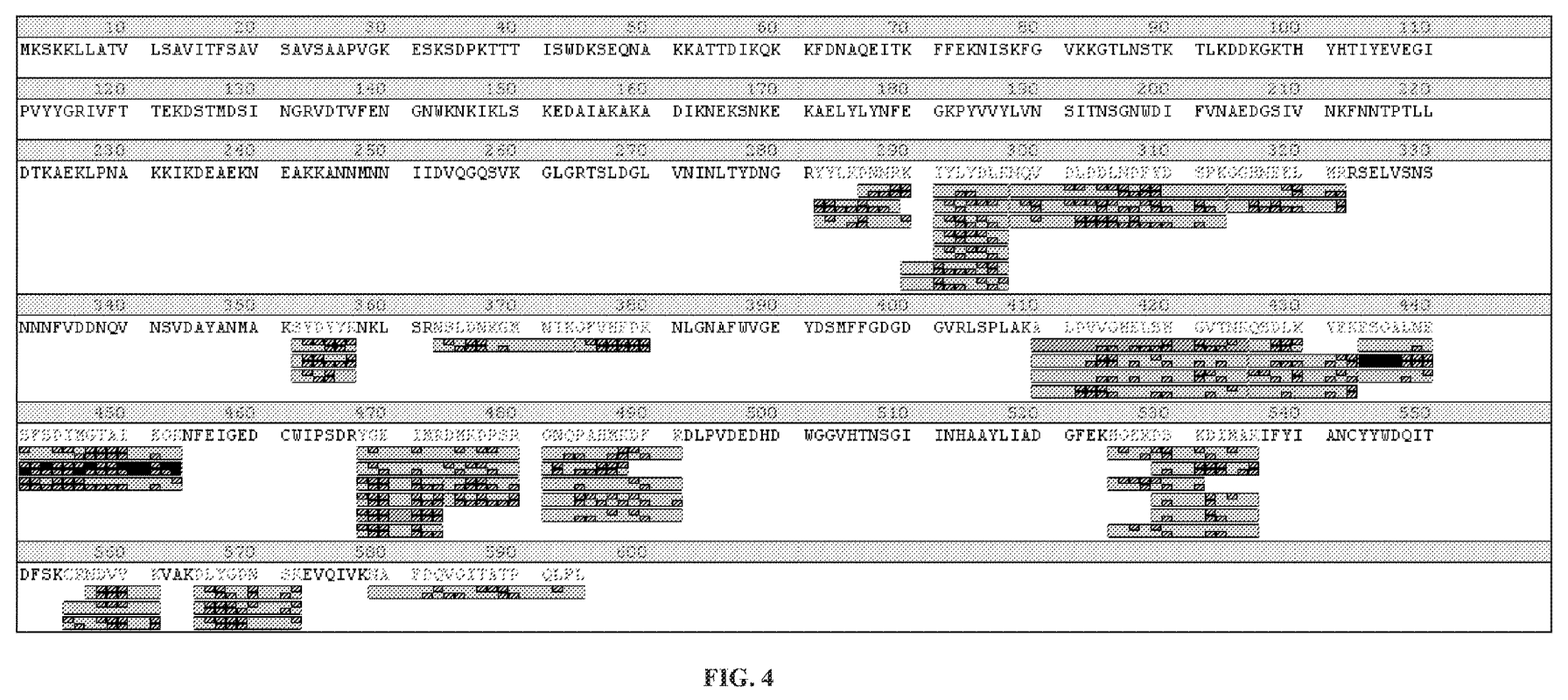

MKSKKLLATV LSAVITFSAV SAVSAAPVGK ESKSDPKTTT ISWDKSEQNA KKATTDIKQK KFDNAQEITK FFEKNISKFG VKKGTLNSTK TLKDDKGKTH YHTIYEVEGI

PVYYGRIVFT TEKDSTMDSI NGRVDTVFEN GNWKNKIKLS KEDAIAKAKA DIKNEKSNKE KAELYLYNFE GKPYVVYLVN SITMSGNWDI FVNAEDGSIV NKFNNTPTLL

DTKAEKLPNA KKIKDEAEKN EAKKAMNMMN IIDVQGQSVK GLGRTSLDGL VNINLTYDNG

NMNFVDDNQV NSVDAYANMA KL SR MLGNAFUVGE YDSMFFGDGD GVRLSPLAKA

CWIPSDRVGK WGGVHTNSGI IMHAAYLIAD GFEK ANCYYDQIT

DFSKC

FIG. 4

MKSKKLLATV LSAVIITFSTV SAVYAAPVGK ESKVEPKTTT ITWEKNEQNT KKAATDITEK K░░░░░░░ FFEKNISKFG VQKGSLKNTK TVKDEKGKTN YHMIYEVEGI
PVYYGRIVFT TEKDSEMDSI NGRIDTVFEN GNWKNKIKLS KEDAIAKAKN DIKDEKATSK KTDLYLYMFE GKPYVYLVD LITDNGSWTV FVNAEDGSIV NKFMNTPTLI
DTKDQKLPNA KKIKDEAKKA SNANNVIDVQ GQSVKGVGKT SLDGLWNIDV TYGNGKYYLK DSNKW░░░░ ░░░░░░░░░ ░░░░░░░░░ ░░L░░░SELI SNYNNNFIAN
NQVNSVDAYV NTNKY░░░░ NKLMNR░░░░ ░░░░░░░░ ░░NYGMAFW VGPYDGMFFG DGDGIYFSSL AKSLDVVGHE LSHGVTNKES NLKY░░░░░ L░░░░░░░
░░░░░░░░ GEDCWVAGGV MR░░░░░░ G░░░░░░░░ YKTMNDDNGG VHITNSGIINH AAYLVADGIE KTGAKNSK░ ░░░░░░░░ V░░░░░░░ ░░░░░░░░
░░░░░░░░ ░░IVEK░░░ ░░░░░░░

```
scBoNTAS wt       KLLCVRGIITSKTKSLDKGYNKALNDLCIKV
scBoNTAS Throm    KLLCVRGIITS.T.SLVPRGS.ALNDLCIKV
scBoNTAS Res      KLLCV.GIITS.T.SLVP.GS.ALNDLCIKV
scBoNTAS (GGSG)2  KLLCGGSG...............GSGGCIKV
scBoNTAS CGS-C    KLL.G..........................S.IKV
scBoNTAS FQWYI    KLLCFQW.................YICIKV
```

FIG. 7B scBoNTAS wt / scBoNTAS Throm — 116kDa, 66kDa, 45kDa scBoNTAS Res / scBoNTAS (GGSG)2 — 116kDa, 66kDa, 45kDa scBoNTAS (-CGS-C) / scBoNTAS (FQWYI) — 116kDa, 66kDa, 45kDa

FIG. 7C

% Abbau scCNT vs t[min]

— ScBoNTAS wt
— ScBoNTAS Throm
— ScBoNTAS Res
— ScBoNTAS (GGSG)2
— ScBoNTAS (-CGS-C)
— ScBoNTAS FQWYI

METHODS FOR THE MANUFACTURE OF PROTEOLYTICALLY PROCESSED POLYPEPTIDES

CROSS-REFERENCE TO RELATED APPLICATIONS

This application is a continuation of U.S. application Ser. No. 16/105,120, filed Aug. 20, 2018, which in turn is a continuation of U.S. application Ser. No. 14/423,222, filed Feb. 23, 2015, now U.S. Pat. No. which is a U.S. national stage filing of International Patent Application No. PCT/EP2012/073283, filed Nov. 21, 2012.

REFERENCE TO SEQUENCE LISTING

The instant application contains a Sequence Listing that has been submitted electronically in ASCII format and is hereby incorporated by reference in its entirety. Said ASCII copy, created on Jul. 14, 2020, is named 16928107SeqList.txt and is 29,713 bytes in size.

BACKGROUND OF THE INVENTION

The present invention relates to a novel proteolytically active polypeptide and various uses of the polypeptide in screening and manufacturing methods.

*Clostridium botulinum* and *Clostridium tetani* produce highly potent neurotoxins, i.e. botulinum neurotoxins (BoNTs) and tetanus neurotoxin (TeNT), respectively. These clostridial neurotoxins (CNTs) specifically bind to neuronal cells and disrupt neurotransmitter release. *Clostridium botulinum* secretes seven antigenically distinct serotypes designated A to G of the botulinum neurotoxin (BoNT). All serotypes together with the related tetanus neurotoxin (TeNT) secreted by *Clostridium tetani*, are $Zn^{2+}$-endoproteases that block synaptic exocytosis by cleaving proteins involved in the formation of the SNARE complex controlling cellular membrane fusion. CNTs cause the flaccid muscular paralysis seen in botulism and tetanus. In addition, CNT activity has been shown to affect glandular secretion. These physiological effects of CNTs on muscular and glandular activity are increasingly used in various therapeutic and cosmetic applications. Botulinum neurotoxin of serotype A (BoNT/A) was approved for human use in the United States in 1989 for the treatment of strabism, blepharospasm, and other disorders. It is commercially available as a botulinum neurotoxin A protein preparation, for example, under the tradename BOTOX (Allergan Inc.) and under the tradename DYSPORT (Ipsen Ltd). For therapeutic application, a complex comprising the neurotoxin and additional bacterial proteins is injected directly into the muscle to be treated. At physiological pH, the toxin is released from the protein complex (Eisele et al. 2011, Toxicon 57(4):555-65.) and the desired pharmacological effect takes place. An improved BoNT/A preparation being free of complexing proteins is available under the tradenames XEOMIN or Bocouture (Merz Pharmaceuticals GmbH, Frankfurt/Germany). The effect of BoNT is only temporary, which is the reason why repeated administration of BoNT is usually required to maintain a therapeutic affect.

Each CNT is initially synthesised as an inactive single chain polypeptide. In the case of BoNT, the neurotoxin polypeptide has a molecular weight of approximately 150 kDa. The posttranslational processing of this single chain polypeptide involves limited proteolysis in an exposed region called loop (see table 1) and the formation of a nearby disulfide bridge. Active di-chain neurotoxin consists of two cleavage products resulting from the proteolytic hydrolysis of the single chain precursor polypeptide: an N-terminal light chain of approx. 50 kDa and a heavy chain of approx. 100 kDa linked by a disulfide bond. CNTs structurally consist of three domains, i.e. the catalytic light chain, the heavy chain encompassing the translocation domain (N-terminal half) and the receptor binding domain (C-terminal half) (cf. Krieglstein 1990, Eur J Biochem 188: 39; Krieglstein 1991, Eur J Biochem 202: 41; Krieglstein 1994, J Protein Chem 13: 49; Lacy et al., 1998, Nat. Struct. Biol. 5(10):898-902). Depending on the number of cleavage sites present in the single chain between the amino acid residues forming the catalytic domain and the amino acid residues forming the translocation domain, endopeptidase activity can give rise to two large cleavage products, i.e. the light and the heavy chain and, in addition, characteristic short peptides representing the former loop region, bridging in the single chain of the neurotoxin what is to become the light and the heavy chain (cf. table 1, below).

The purification of the CNTs from the fermentation solution is a particular challenge, since the neurotoxins are contained therein as a mixture of unprocessed, partially processed and fully processed polypeptides, all of which have very similar biochemical and physical properties. Partially processed neurotoxins are typically generated, if the endoproteolytic activity has hydrolysed the peptide bond between the light chain and the loop, while the peptide bond between the loop and the N-terminus of the heavy chain is still intact. Moreover, partially processed neurotoxin can also be created if the endoproteolytic activity has released the loop peptide from the heavy chain, while the peptide bond between the loop peptide and the C-terminus of the light chain has not yet been hydrolysed. Depending on the conditions of fermentation and the type of neurotoxin, the fully processed polypeptide which is devoid of the loop peptide can be contaminated significantly, with between 5% to 90% partially processed or unprocessed polypeptide. Yet in some cases, the neurotoxin is mainly unprocessed and, prior to therapeutic use, needs to be treated with an endopeptidase in order to become biologically active.

The prior art describes various attempts to treat clostridial neurotoxins with heterologous proteases in order to reduce the amount of unprocessed or partially processed precursor protein. The protease most widely used for activation of clostridial neurotoxins, Trypsin, while being useful for activating clostridial neurotoxins of serotypes B (BoNT/B) and E (BoNT/E) (DasGupta & Sugiyama 1972, Biochem. Biophys. Res. Commun. 48: 108-112; Kozaki et al., 1974, Infect. Immun. 10: 750-756) appears to produce secondary products, presumably by proteolytic action near the C-terminus of the heavy subunit of BoNT/A and, thus, appears to destroy toxin binding to its cellular receptor (Shone et al., 1985, Eur. J. Bioch. 151: 75-82). More specific cleavage products are theoretically expected from endogenous proteases, isolated from the native host, such as *C. botulinum* producing BoNT/A. Accordingly, various attempts have been made to isolate from the native host cell the endogenous protease involved in proteolytic activation of clostridial neurotoxins. Dekleva & DasGupta (Dekleva & DasGupta, 1989, Biochem. Biophys. Res. Commun. 162: 767-772) purified from cultures of *C. botulinum* producing BoNT/A a fraction capable of proteolytically cleaving BoNT/A into a heavy and a light subunit. Later studies of the same authors further characterised the endogenous protease isolated from *C. botulinum* (Dekleva & DasGupta, 1990, J. Bact. 172: 2498-2503) and revealed a 62 kDa protein, composed of a 15.5 kDa polypeptide and a 48 kDa polypeptide. However, the observation of considerable fragmentation of CNTs after limited exposure to the 62 kDa protein of Dekleva & DasGupta suggests that the isolated protease may not be the unidentified proteolytic enzyme responsible for the activation of CNTs in clostridial cell cultures and during infection. In fact, others have recently suggested that Clostripain, also designated clostridiopeptidase B (Mitchel & Harrington, 1968, JBC 243: 4683-4692), might be involved in the specific activation of CNTs (Sebaihia et al., 2007, Genome Res. 17(7):1082-1092; WO2009/014854). Interestingly, the structure and substrate specificity of this enzyme are reminiscent of those of the secreted alpha-clostripain from Clostridium histolyticum (Dargatz et al. 1993), a homolog (74% amino acid identity) of which is present in C. botulinum (CB01920). The C. histolyticum alpha-clostripain is a cysteine endopeptidase with strict specificity for the arginyl bond. It is synthesized as an inactive prepro-enzyme that undergoes an autocatalytic cleavage to generate 15.4- and 43-kDa polypeptides, which associate to form a heterodimeric active enzyme (Dargatz et al. 1993). Both the C. histolyticum alphaclostripain and the C. botulinum 62-kDa protease require a reducing agent and calcium for full activity and are susceptible to the same protease inhibitors. These data strongly suggest that the C. botulinum ortholog of alpha-clostripain (CBO1920) is the endogenous protease responsible for the proteolytic nicking of the neurotoxin of C. botulinum. A gene encoding clostripain (CPE0846) is also present in C. perfringens, and has been found to be positively regulated by the two-component system VirR/VirS (Shimizu et al. 2002b).

Till this day, however, further conclusive experimental evidence is missing and a protease capable of efficiently converting the single chain precursor CNTs into the authentic mature cleavage products, i.e. the di-chain neurotoxin, is still not available in the art. The present invention solves one or more of the above-described problems.

Means and methods for reducing the amount of unprocessed and/or partially processed neurotoxin polypeptides and thereby improving the quality of neurotoxin preparations are highly desirable but not yet available. Thus, a technical problem underlying the present invention may be seen as the provision of means and methods for improving the manufacture of neurotoxin polypeptides by complying with the aforementioned needs. The technical problem is solved by the embodiments characterised in the claims and herein below.

BRIEF DESCRIPTION OF THE DRAWINGS

FIG. 4 depicts an ESI-MS/MS analysis of the purified 38.6 kDa protein from Lot TE311206, as described in Example 2. The protein was identified as NT02CB1446/CB01444.

FIG. 5 depicts an ESI-MS/MS analysis of the purified 37.3 kDa protein from sample TE301009, as described in Example 2. The protein was identified as NT02CB1447/CB01445.

FIG. 7A depicts the sequences of the wild-type BoNT/A activation loop and various deletion mutations thereof.

FIG. 7B depicts an SDS-PAGE analysis of the ability of purified nBH to cleave wild-type single-chain BoNT/A and the mutants from FIG. 7A (~150 kDa) into separate heavy (~100 kDa) and light (~50 kDa) chains over time (0, 30, 60, 120, 180, and 240 minutes).

FIG. 7C is a densitometry plot of the intensity of the ~150 kDa bands shown in FIG. 7B over time. The plot shows that the amount of wild-type single-chain BoNT/A or mutants thereof in the samples decreases over time in the presence of nBH.

FIG. 8A depicts a MS/MS analysis of the ~50 kDa product formed after cleavage of wild-type single-chain BoNT/A by nBH.

FIG. 8B depicts a MS/MS analysis of the ~100 kDa product formed after cleavage of wild-type single-chain BoNT/A by nBH.

FIG. 10A is a SDS-PAGE gel analysis of elution fractions (E1-E7) taken from the purification of inactive recombinant BH by affinity chromatography from cell lysate, as described in Example 6. The lane marked "SS34" contains clarified lysate. The lane marked "LMW" contains the molecular weight ladder (116 kDa, 66 kDa, 45 kDa, 35 kDa, and 25 kDa). The lane marked "TD" contains proteins that did not bind to the column. The lane marked "W" contains the wash, i.e., residual components that did not bind to the column.

FIG. 10B is a SDS-PAGE gel analysis of the outcome of incubating inactive BH with single-chain BoNT/A, as described in Example 6. The lanes marked "0" contain samples taken at time 0 whereas the lanes marked "37°" contain samples taken after incubation of the reaction mixture at "37°" for 1 hour. The lanes marked "E" contain inactive BH. The lanes marked "A+E, 37°" contain single-chain BoNT/A and inactive BH incubated for 1 hour at 37°. The lane marked "LMW" contains the molecular weight ladder (same as in FIG. 10A). The absence of bands at ~50 kDa and ~100 kDa, suggests that the inactive BH is inactive at these conditions.

DETAILED DESCRIPTION OF THE INVENTION

Figure 1:
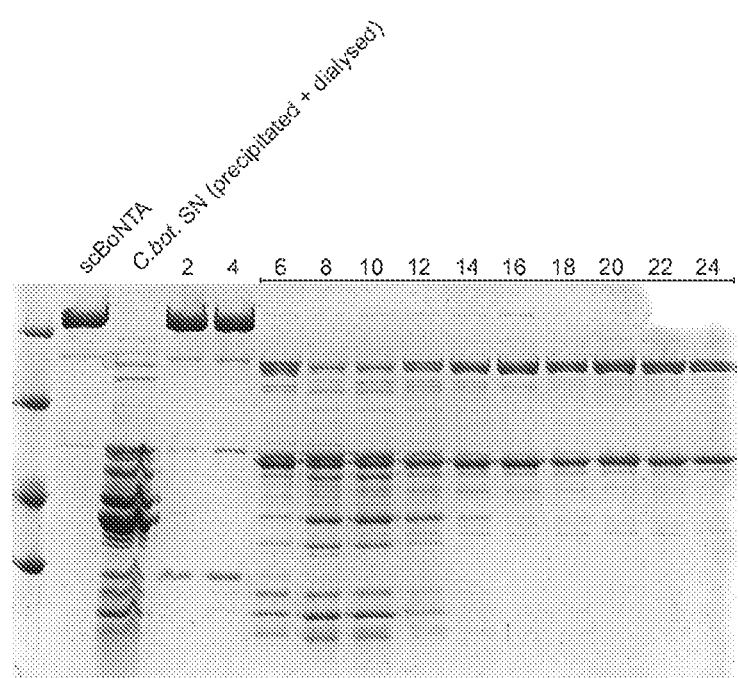
FIG. 1 depicts a 10% SDS-PAGE gel analysis of enzymatic activity in cleared C. botulinum cell lysate supernatant fractions collected following ion exchange chromatography (IEC) as described in Example 1. Collected fractions were incubated with single-chain BoNT/A and loaded onto the gel (lane marked as "2" contains the second fraction collected, lane marked as "4" contains the fourth fraction collected, etc.). The left-most lane of the gel contains low molecular weight marker (LMW): 116 kDa, 66 kDa, 45 kDa, and 35 kDa. The second-to-the-left lane contains single chain BoNT/A. The third-to-the-left lane contains cleared C. botulinum cell lysate. The lanes containing the sixth to $24^{th}$ fractions show that single-chain BoNT/A had been converted into separate heavy (~100 kDa) and light (~50 kDa) chains.

The present invention relates in one aspect to a proteolytically active polypeptide which comprises a polypeptide sequence having at least 50% sequence identity with the sequence of SEQ ID NO: 1. In another aspect, the present invention relates to a proteolytically active polypeptide consisting of a polypeptide sequence having at least 50% sequence identity with the sequence of SEQ ID NO: 1. In another aspect, the present invention relates to a proteolytically active polypeptide consisting of a polypeptide sequence as shown in SEQ ID NO: 1.

The term "proteolytically active polypeptide" as used herein refers to the catalytic function of the polypeptide of the present invention and means that the polypeptide of the present invention is capable of hydrolysing a peptide bond. In one aspect, "proteolytically active polypeptide" refers to a polypeptide that is capable of hydrolysing a polypeptide comprising an amino acid sequence selected from any one of SEQ ID NOs: 4 to 25. The term "proteolytically inactive polypeptide" as used herein refers to the catalytic function of the polypeptide of the present invention and means that the polypeptide of the present invention is incapable of hydrolysing a peptide bond.

The skilled person can determine whether a polypeptide according to the sequence definition mentioned herein is a polypeptide according to the present invention, by testing the proteolytic activity of said polypeptide. An assay or test system for determining proteolytic activity comprises contacting a polypeptide which comprises a polypeptide sequence having at least 50% sequence identity with the sequence of SEQ ID NO: 1 with a test substrate. A test substrate is typically a polypeptide which is known to be cleavable by the polypeptide of the present invention. Preferably, the test substrate is a CNT such as BoNT or a fragment thereof. The test substrate can be e.g. uncleaved/unprocessed BoNT, designated herein as "scBoNT" and can be e.g. of serotype A, B, C1, D, E, F or G (e.g. "scBoNT/A", "scBoNT/B" etc.) or the test substrate can be tetanus neurotoxin. Alternatively, the test substrate can be a fragment of a clostridial neurotoxin, said fragment comprising an amino acid sequence selected from any one of SEQ ID NOs: 4 to 25. The fragment can be a polypeptide of 50 or more amino acid residues or a peptide of up to 49 amino acid residues. As used throughout the present specification, the term "polypeptide" refers to molecules with 50 or more amino acid residues, whereas the term "peptide" refers to molecules with 2 to 49 amino acid residues. In one aspect, the test substrate is a soluble neurotoxin fragment called LHN comprising the light chain polypeptide, the exposed loop peptide region and the N-terminal half of the heavy chain polypeptide, the translocation domain HN. In another aspect, the test substrate is or comprises a peptide selected from any one of SEQ ID NOs: 4 to 25 (cf. table 1). In yet another aspect, the test substrate is a chimeric neurotoxin comprising amino acid residues derived from two or more serotypes.

An assay for determining the proteolytic activity would typically comprise a step of determining the degree of conversion of the test substrate into its cleavage product(s). The observation of one or more cleavage product(s) generated after contacting the polypeptide with the test substrate or the observation of an increase in the amount of cleavage product(s) is indicative of proteolytic activity of the polypeptide. Said step of determining may involve comparing substrate and cleavage product(s). Said comparing may involve determining the amount of substrate and/or the amount of one or more cleavage product(s) and may also involve calculating the ratio of substrate and cleavage product(s). In addition, the assay for determining the proteolytic activity may comprise a step of comparing a test sample with a reference sample, wherein the reference sample typically comprises (a) a polypeptide which comprises a polypeptide sequence having at least 50% sequence identity with the sequence of SEQ ID NO: 1 and which is known to be proteolytically active and (b) a test substrate known to be cleavable by the polypeptide of (a). In one aspect, the assay for determining the proteolytic activity comprises separating substrate and cleavage product(s) by electrophoresis or by column chromatography and, optionally, a spectrometric analysis. It may be convenient to label the test substrate with one or more labels in order to more easily detect decrease of test substrate and/or increase of product(s). The term "label", as used herein, means detectable marker and includes e.g. radioactive label, antibody, fluorescent label. The amount of test substrate and/or cleavage product may be determined e.g. by methods of autoradiography or spectrometry, including methods based on energy resonance transfer between at least two labels. Alternatively, immunological methods such as western blot or ELISA may be used for detection. A preferred assay for determining the proteolytic activity of the polypeptide of the present invention is described herein below in the Examples illustrating the invention. In a particularly preferred embodiment of the present invention, a polypeptide is proteolytically active, if more than 20%, preferably more than 95% of test substrate is converted into the cleavage products such as the light chain and the heavy chain in 120 min at 37° C. using a buffer selected from 100 mM Tris-HCl, pH 8.0 or PBS (50 mM $Na_2HPO_4$, 150 mM NaCl, pH 7.4). The same conditions apply, if the test substrate is not a full length neurotoxin but, instead, e.g. a fragment of the full length neurotoxin or a derivative of the neurotoxin. It is apparent that the cleavage products will differ in this case. However, the skilled person can quantify the corresponding cleavage products. In another aspect, typically, 100 ng of proteolytically active polypeptide and a molar ratio of 1:100 with regard to the substrate are used in the assay. In yet another aspect, a sample may be taken at intervals in order to follow the catalytic activity over time. The assay may be modified, e.g. by using multiple amounts of the proteolytically active polypeptide.

SEQ ID NO: 2 shows the polypeptide sequence of a proteolytically inactive polypeptide derived from a *Clostridium botulinum* strain ATCC 3502, GenBank accession No: "CAL82988.1", having an amino acid length of 581 residues. SEQ ID NO: 1 shows a proteolytically active derivative of SEQ ID NO: 2, lacking amino acid residues 1 to 248 of SEQ ID NO: 2.

The term "polypeptide which comprises a polypeptide sequence having at least 50% sequence identity with the sequence of SEQ ID NO: 1" refers to a polypeptide which has at least 50% sequence identity with the sequence of SEQ ID NO: 1. In addition, the term refers to a polypeptide which comprises a polypeptide sequence having at least 50% sequence identity with the sequence of SEQ ID NO: 1. Said polypeptide may have additional amino acids, for example at an internal position or N- or C-terminal to the sequence shown in SEQ ID NO: 1 or at an internal position or N- or C-terminal to a amino acid sequence which is at least 50% identical with sequence of SEQ ID NO: 1, wherein a methionine may be present at the N-terminus of the polypeptide. In addition, the term refers to a polypeptide lacking one or more amino acid residues, for example at an internal position or at the N- or C-terminus of the sequence shown in SEQ ID NO: 1 or at an internal position or the N- or C-terminus of a sequence which is at least 50% identical in sequence to SEQ ID NO: 1.

The term "sequence identity" as used herein refers to determination of the identity between a reference amino acid sequence and a query sequence wherein the sequences are aligned so that the highest order match is obtained, and which can be calculated using published techniques or methods codified in computer programs such as, for example, BLASTP, BLASTN, FASTA (Altschul 1990, J Mol Biol 215: 403). The percent identity values are in one aspect calculated over the entire amino acid sequence. In another aspect, sequence identity is calculated over a sequence length of up to 50aa residues, up to 100aa, up to 150aa, up to 250aa, 300aa, 350aa, 400aa, 450aa, 500aa, or 550aa residues. In another aspect, sequence identity is calculated over at least 50aa residues, at least 100aa, at least 150aa or at least 250aa residues. In preferred embodiments, sequence identity is determined over the entire length of SEQ ID NO: 1 or 2, i.e. over a length of 333aa or 581aa, respectively. A series of programs based on a variety of algorithms is available to the skilled worker for comparing different sequences. In this context, the algorithms of Needleman and Wunsch or Smith and Waterman give particularly reliable results. To carry out the sequence alignments and calculate the sequence identity values recited herein, the commercially available program DNASTAR Lasergene MegAlign version 7.1.0 based on the algorithm Clustal W was used over the entire sequence region with the following settings: Pairwise Alignment parameters: Gap Penalty: 10.00, Gap Length Penalty: 0.10, Protein weight matrix Gonnet 250, which, unless otherwise specified, shall always be used as standard settings for sequence alignments.

The term "at least 50% sequence identity" as used herein means at least 50%, at least 55%, at least 60%, at least 65%, at least 70%, at least 75%, at least 80%, at least 85%, at least 90%, at least 95% or 100%.

The proteolytically active polypeptide of the present invention may have the same number of amino acids as the reference polypeptide sequence as shown in SEQ ID NO: 1. Also comprised by the present invention are polypeptides having additional or less amino acid residues. In one aspect, the proteolytically active polypeptide of the present invention is or comprises a truncation mutant of SEQ ID NO:1 or 2 or of a polypeptide having at least 50% sequence identity with the sequence of SEQ ID NO: 1 or 2. The truncation mutant of SEQ ID NO: 2 may for example lack one or more amino acid residues N-terminal to amino acid position 249. A truncation mutant may be an N- or C-terminal truncation mutant and/or an internal truncation mutant that is proteolytically active. In one aspect, said truncation mutant of SEQ ID NO:2 lacks amino acid positions 1 to 248 of SEQ ID NO: 2. In another aspect, the truncation mutant of SEQ ID NO: 2 is a C-terminal truncation mutant. In one aspect, the truncation mutant lacks up to 1, 2, 3, 4, 5, 6, 7, 8, 9, 10, 15, 20, 50, 100, 150 or up to 170 consecutive amino acid residues. In another aspect, the proteolytically active polypeptide of the present invention has an amino acid length of at least 200aa residues, of at least 250aa residues, of at least 300aa residues or of at least 333aa residues. In another aspect, the proteolytically active polypeptide of the present invention has up to 333aa residues, up to 350aa residues, up to 573 residues, up to 581aa residues, up to 592aa residues, up to 600aa or up to 617aa residues.

In another aspect, the proteolytically active polypeptide of the present invention encompasses a polypeptide comprising additional amino acid residues at the N- or C-terminus and/or at an internal position of the polypeptide chain of SEQ ID NO: 1 or a of a polypeptide sequence having at least 50% sequence identity with the sequence of SEQ ID NO: 1. These additional amino acid residues may comprise up to 5, up to 10 or even up to 200, 300 or up to 400 consecutive amino acid residues. In one aspect, the additional amino acid residues function as an inhibitor of the proteolytic activity. In another aspect, the additional amino acid residues can be removed by a protease. In another aspect, additional residues inhibiting the proteolytic activity of the polypeptide of the present invention are excluded. The additional amino acid residues may be flanked by one or more protease cleavage sites. In another aspect, the additional amino acid sequence functions as a detectable tag and/or allows binding to a solid support.

In another aspect, the polypeptide chain of SEQ ID NO: 1 or a of a polypeptide sequence having at least 50% sequence identity with the sequence of SEQ ID NO: 1 is modified by exchanging one or more amino acid residues. The term "exchanging", as used herein, means replacing an amino acid with a different amino acid. For example, up to 1aa, 2aa, 3aa, 4aa, 5aa, 6aa, 7aa, Baa, 9aa, 10aa, 15aa, 20aa or up to 50aa may be replaced within the polypeptide sequence. The exchanges may involve conservative or non-conservative amino acid changes, aiming e.g. at increasing or decreasing substrate binding or proteolytic activity of the polypeptide of the present invention.

In one aspect, the proteolytically active polypeptide of the present invention encompasses a polypeptide that is capable of hydrolysing a substrate into two or more native cleavage product(s). In another aspect, the polypeptide of the present invention hydrolyses the substrate into two or more cleavage products which differ from the native cleavage products. The term "native cleavage products" or "native products" as used herein refers to products, which are identical in amino acid sequence when compared to products generated from the same substrate in wildtype cell cultures, from which the substrate originates. In one aspect the cleavage product is the di-chain neurotoxin of a botulinum neurotoxin or of tetanus neurotoxin, in another aspect the di-chain neurotoxin is a neurotoxin isolated from C. botulinum of serotype A, B, C1, D, E, F or G. In yet another aspect, said di-chain neurotoxin is a native di-chain neurotoxin.

Table 1 shows the precursor, the native di-chain neurotoxin of TeNT and of BoNT/A-G and identifies the exposed loop comprising the amino acid sequence cleaved by the polypeptide of the present invention.

| Toxin | exposed loop | LC | $H_N$ | $H_{CN}$ | $H_{CC}$ |
|---|---|---|---|---|---|
| BoNT/A1 | SEQ ID NO: 4 | M1-K438 | A449-N872 | I873-S1092 | N1093-L1296 |
| BoNT/A2 | SEQ ID NO: 5 | M1-K438 | A449-N872 | I873-S1092 | N1093-L1296 |
| BoNT/A3 | SEQ ID NO: 6 | M1-K434 | A445-N868 | I869-S1088 | N1089-L1292 |
| BoNT/A3 | SEQ ID NO: 7 | M1-K434 | A445-N868 | I869-S1088 | N1089-L1292 |
| BoNT/A4 | SEQ ID NO: 8 | M1-K438 | A449-N872 | I873-S1092 | N1093-L1296 |
| BoNT/A5 | SEQ ID NO: 9 | M1-K438 | A449-N872 | I873-S1092 | N1093-L1296 |
| BoNT/A6 | SEQ ID NO: 5 | M1-K438 | A449-N872 | I873-S1093 | N1094-L1297 |
| BoNT/A7 | SEQ ID NO: 10 | M1-K438 | A449-N872 | I873-S1092 | N1093-L1296 |
| BoNT/B1 | SEQ ID NO: 11 | M1-K441 | A442-I860 | L861-S1079 | Y1080-E1291 |
| BoNT/B2 | SEQ ID NO: 12 | M1-K441 | A442-I860 | L861-S1079 | Y1080-E1291 |
| BoNT/B3 | SEQ ID NO: 12 | M1-K441 | A442-I860 | L861-S1079 | Y1080-E1291 |
| BoNT/B4bv | SEQ ID NO: 11 | M1-K441 | A442-I860 | L861-S1079 | Y1080-E1291 |
| BoNT/B5nP | SEQ ID NO: 13 | M1-K441 | V442-I860 | L861-S1079 | Y1080-E1291 |
| BoNT/B6 | SEQ ID NO: 11 | M1-K441 | A442-I860 | L861-S1079 | Y1080-E1291 |
| BoNT/C1 | SEQ ID NO: 14 | M1-R444 | T450-I868 | N869-L1092 | Q1093-E1291 |
| BoNT/CD | SEQ ID NO: 14 | M1-R444 | T450-I868 | N869-Q1083 | I1084-E1280 |
| BoNT/D | SEQ ID NO: 15 | M1-K442 | D446-I864 | N865-Q1079 | I1080-E1276 |
| BoNT/DC | SEQ ID NO: 16 | M1-K442 | D446-I864 | N865-L1088 | Q1089-E1285 |
| BoNT/E1-E5 | SEQ ID NO: 17 | M1-K419 | S424-I847 | K848-P1067 | N1068-K1252 |
| BoNT/E6 | SEQ ID NO: 18 | M1-K419 | S424-I847 | K848-P1067 | N1068-K1252 |
| BoNT/F1 | SEQ ID NO: 19 | M1-R435 | A440-I866 | K867-P1085 | D1086-N1278 |
| BoNT/F2 | SEQ ID NO: 20 | M1-R435 | Q440-I866 | K867-P1088 | D1089-E1280 |
| BoNT/F3 | SEQ ID NO: 20 | M1-R435 | Q440-I866 | K867-P1088 | D1089-E1279 |
| BoNT/F4 | SEQ ID NO: 21 | M1-R435 | A440-I866 | K867-P1085 | D1086-E1277 |
| BoNT/F5 | SEQ ID NO: 22 | M1-K434 | P440-I863 | K864-P1085 | D1086-E1277 |
| BoNT/F6 | SEQ ID NO: 19 | M1-R435 | A440-I866 | K867-P1088 | D1089-E1275 |
| BoNT/F7 | SEQ ID NO: 23 | M1-K427 | N432-I857 | I858-P1076 | D1077-E1268 |
| BoNT/G | SEQ ID NO: 24 | M1-K442 | S447-I865 | S866-S1086 | S1087-E1297 |
| TeNT | SEQ ID NO: 25 | M1-R449 | T456-K883 | S884-L1109 | S1110-D1315 |

It is to be understood that the definitions and explanations of the terms made above and below apply mutatis mutandis for all aspects described in this specification unless otherwise indicated.

The proteolytically active polypeptide of the present invention is suitable for various applications. A commercially relevant application is its use in the production of therapeutic neurotoxins, such as those isolated from C. botulinum. At present, the cell cultures of C. botulinum used for the preparation of commercially available preparations of botulinum neurotoxin are contaminated with significant amounts of partially processed and/or unprocessed neurotoxin, both of which negatively impair, i.e. reduce the specific activity of these pharmaceutical compositions. Using the proteolytically active or activated polypeptide of the present invention for example after lysis of C. botulinum, it will now be possible to treat compositions comprising unprocessed and/or partially processed neurotoxin and, thus, convert these contaminants into fully processed neurotoxin. In consequence, commercial products can be provided with an increased specific activity of the neurotoxin, wherein the total amount of bacterial protein can be reduced, further reducing the patients risk of antibody formation.

In another aspect, the present invention relates to a nucleic acid molecule comprising a nucleic acid sequence encoding the polypeptide of the present invention and, optionally, regulatory elements. The term "regulatory elements" as used herein refers to regulatory elements of gene expression, including transcription and translation, and includes elements such as tata box, promotor, enhancer, ribosome binding site, Shine-Dalgarno-sequence, IRES-region, polyadenylation signal, terminal capping structure, and the like. Said regulatory element may comprise one or more heterologous regulatory elements or one or more homologous regulatory elements. A "homologous regulatory element" is a regulatory element of a wildtype cell, from which the nucleic acid molecule of the present invention is derived, which is involved in the regulation of gene expression of the nucleic acid molecule or the polypeptide in said wildtype cell. The present invention also encompasses nucleic acid molecules comprising heterologous regulatory elements. The term "heterologous regulatory element" is a regulatory element which is not involved in the regulation of gene expression of the nucleic acid molecule or the polypeptide in said wildtype cell. Also regulatory elements for inducible expression, such as inducible promoters, are encompassed. The nucleic acid molecule can be, for example, hnRNA, mRNA, RNA, DNA, PNA, LNA, and/or modified nucleic acid molecules. The nucleic acid molecule can be circular, linear, integrated into a genome or episomal. Also concatemers coding for fusion proteins comprising three, four, five, six, seven, eight, nine or ten polypeptides of the present invention are encompassed. Moreover, the nucleic acid molecule may contain sequences encoding signal sequences for intracellular transport such as signals for transport into an intracellular compartment or for transport across the cellular membrane.

In another aspect, the present invention relates to a vector comprising a nucleic acid molecule according to the nucleic acid molecule of the present invention. A vector may be suitable for in vitro and/or in vivo expression of the polypeptide of the present invention. The vector can be a vector for transient and/or stable gene expression. In one embodiment the vector furthermore comprises regulatory elements and/or selection markers. Said vector in one embodiment is of virus origin, in another embodiment of phage origin, in yet another embodiment of bacterial origin.

In another aspect, the present invention relates to a cell comprising the nucleic acid molecule or the vector of the present invention. The term "cell" as used herein, encompasses prokaryotic and/or eukaryotic cells suitable to express said nucleic acid molecule or said vector and in particular the polypeptide of the invention. Said cell may be a host cell not expressing the polypeptide of the present invention or a homolog thereof. The term "homolog" as used herein refers to a polypeptide comprising a polypeptide sequence having at least 50% sequence identity with the sequence of SEQ ID NO: 1. However, also encompassed by the present invention are cells, in particular wildtype cells, expressing the polypeptide of the present invention or a homolog thereof. In a particular aspect, the cell of the present invention is selected from *C. botulinum, C. butyricum, C. baratii* and *C. tetani*. In a preferred aspect, the cell is *C. botulinum* of serotype A, B or F. In another aspect, said cell is the Hall strain (ATCC 3502) of *C. botulinum*. In another aspect, said cell is the BoNT/A producing strain ATCC 19397 also known as NCTC 4587 and NCTC 7272 of *C. botulinum*. In another aspect, said cell is the BoNT/A producing strain NCTC 2916 of *C. botulinum*. In another aspect, said cell are the BoNT/A2 producing strains Kyoto-F and Mauritius/NCTC 9837 of *C. botulinum*. In another aspect, said cell is the BoNT/A3 producing strain A254 Loch Maree/NCTC 2012 of *C. botulinum*. In another aspect, said cell is the BoNT/A4 and B producing strain CDC657 of *C. botulinum*. In another aspect, said cell is the BoNT/A5 and B3' producing strain H04402 065 of *C. botulinum*. In another aspect, said cell is the BoNT/B1 producing strain Okra/NCTC 7273 of *C. botulinum*. In another aspect, said cell is the BoNT/B and F producing strain CDC4013/NCTC 12265 of *C. botulinum*. In another aspect, said cell is the BoNT/F1 producing strain Langeland/NCTC 10281 of *C. botulinum*. In another aspect said cell is *Clostridium sporogenes, Clostridium perfringens, Clostridium acetobutylicum, B. cereus, B. thuringiensis, B. mycoidis, B. thermoproteolyticus, B. anthracis, B. megaterium, B. subtilis, E. coli*, or a yeast cell. In one aspect, the polypeptide of the present invention is modified inside the cell (i.e. glycosylated, phosphorylated, processed by proteases, etc.). Modification also includes the addition of non-proteinaceous co-factors including metal-ions. Cells comprising the proteolytically inactive polypeptide described above, any intermediate polypeptide product, as well as the final proteolytically active polypeptide disclosed herein are encompassed by this invention. Also encompassed by the present invention are cells comprising an inducer of expression of the polypeptide of the present invention. Such an inducer of expression may be a nucleic acid molecule or a polypeptide or a chemical entity, including a small chemical entity, having the effect of increasing the amount or activity of proteolytically active polypeptide of the present invention in cell cultures or lysates thereof. The inducer of expression may e.g. increase transcription or translation of a nucleic acid molecule encoding the polypeptide of the present invention. Alternatively, the inducer of expression may be a compound capable of activating the proteolytically inactive polypeptide SEQ ID NO:2 or a polypeptide comprising a polypeptide sequence having at least 50% sequence identity with the sequence of SEQ ID NO: 2. In one aspect, said cell comprises an inducer that is a proteolytically active polypeptide capable of removing inhibitory amino acid residues from the N-terminus of said polypeptide. The inducer may be, for example, expressed by recombinant means known to the person skilled in the art. Alternatively, the inducer may be isolated from a cell, e.g. a clostridial cell.

The present invention also relates to the use of the nucleic acid molecule of the present invention for the manufacture of the proteolytically active polypeptide of the present invention.

In a related aspect, the present invention relates to a method for the manufacture of a proteolytically active polypeptide, comprising the steps of: (a) chemically synthesizing or translating from a nucleotide sequence a polypeptide, comprising a polypeptide sequence having at least 50% sequence identity with the sequence of SEQ ID NO: 1; and (b) purifying the polypeptide of step (a).

The term "chemically synthesizing" means synthesizing polypeptides by chemical means. Such methods are reviewed for example in Nilsson et al., Ann. Rev. Biophys. Biomol. Struct. 2005. 34:91-118. The term "purifying the polypeptide" means removing from a mixture comprising the polypeptide of the present invention compounds other than said polypeptide. The term also means removing the polypeptide of the present invention from a mixture comprising compounds other than said polypeptide. In a particular aspect, the term means separating the proteolytically active polypeptide from its proteolytically inactive precursor.

The nucleic acid may be translated in a cell or in a cell free system. Various systems for cell free translation are available to the skilled person. The present invention encompasses, for example, the translation in a cell-free protein translation system comprising rabbit reticulocyte lysate, wheat germ lysate, E. coli lysate, or other cellular lysates, for example lysates generated from C. botulinum and the like. Also encompassed is translating the polypeptide of the present invention from the nucleotide sequence of the present invention or the vector of the present invention. Transcription may be regulated or controlled by one or more heterologous regulatory elements or by homologous regulatory elements. Also encompassed by this aspect of the present invention is the translation in a wildtype cell, i.e. a cell isolated from nature, such as any known isolate of C. botulinum, C. butyricum, C. baratii, and C. tetani. In a particular aspect, said cell is C. botulinum Hall strain (ATCC 3502). Various standard means and methods are available to the skilled person for bringing a nucleic acid molecule or a vector into the cell and for expressing the polypeptide of the present invention as recombinant protein in a cell. Moreover, the skilled person knows many standard techniques for isolating polypeptides from cells or cell lysates or from cell free expression systems (e.g. Recombinant DNA Principles and Methodologies, J. Green, Marcel Dekker Inc., 1998; The Condensed Protocols: From Molecular Cloning: A Laboratory Manual, Sambrook et al, Cold Spring Harbor Laboratory, 2006; Molecular Cloning: A Laboratory Manual, Sambrook et al., Cold Spring Harbor Laboratory, 2000). Any of these means and methods may be used in the methods of the present invention.

The first polypeptide of the present invention may be translated from a nucleic acid molecule encoding the proteolytically active polypeptide. SEQ ID NO: 26 is an example of such a nucleic acid molecule. Alternatively, said nucleic acid molecule may encode a precursor polypeptide which is proteolytically inactive but which can be converted into the proteolytically active polypeptide of the present invention. SEQ ID NO: 27 is an example of such a nucleic acid molecule. The proteolytically inactive precursor is also designated "inactive BoNTHydrolase", abbreviated iBH. This proteolytically inactive polypeptide may e.g. be activated during or after translation or by contacting, for example, said proteolytically inactive polypeptide with a protease capable of removing inactivating amino acid residues at the N-terminus of the proteolytically inactive polypeptide. An example of a proteolytically inactive polypeptide is the polypeptide represented by SEQ ID NO: 2. Another example is a polypeptide comprising a polypeptide sequence having at least 50% sequence identity with the sequence of SEQ ID NO: 2. The term "inactivating amino acid residues at the N-terminus" in one aspect relates to the first 248aa residues of said polypeptide. In another aspect, this term refers to a fragment of up to 10aa, 50aa, 100aa, 150aa, 200aa, 250aa residues of said polypeptide. Any of these polypeptides are useful in the present invention's method for the manufacture of a proteolytically active polypeptide. In one aspect, the protease capable of removing inactivating amino acid residues from the N-terminus of this polypeptide is isolated e.g. from Clostridium botulinum, Clostridium butyricum, Clostridium baratii, and Clostridium tetani. In another aspect, the protease capable of removing said inactivating amino acid is provided by providing a fractionated or non-fractionated lysate of said cells. Inactivating amino acid residues may be removed by contacting the proteolytically inactive polypeptide with said lysate and incubating until the proteolytically inactive polypeptide is transformed into the proteolytically active polypeptide.

In another aspect of the present invention's method, the polypeptide is translated in a cell. The cell may be a prokaryotic or eukaryotic cell. In one aspect the cell is selected from E. coli, B. subtilis or yeast. Also encompassed by the present invention is the translation of the polypeptide of the present invention in a wildtype cell, i.e. a cell isolated from nature, such as any known isolate of Clostridium botulinum, Clostridium butyricum, Clostridium baratii, and Clostridium tetani. In a particular aspect, said cell is C. botulinum Hall strain (ATCC 3502). In another particular aspect, said cell is the cell of the present invention described herein above.

Translation products obtained by the present invention's method may be purified by various means, all of which are known to the person skilled in the art (e.g. Recombinant DNA Principles and Methodologies, J. Green, Marcel Dekker Inc., 1998; The Condensed Protocols: From Molecular Cloning: A Laboratory Manual, Sambrook et al, Cold Spring Harbor Laboratory, 2006; Molecular Cloning: A Laboratory Manual, Sambrook et al., Cold Spring Harbor Laboratory, 2000). Typical methods of purifying the polypeptide of the present invention may involve spinning of cell lysate, ammonium sulphate precipitation of proteins, resuspension of proteins, centrifugation of resuspended proteins, ion exchange chromatography, size exclusion chromatography, hydrophobic interaction chromatography and the like. Several combinations of such steps, in differing order, may be useful for purifying the polypeptide of the present invention. A preferred method for purifying the polypeptide of the present invention is described in the Examples which illustrate the invention.

In one aspect, the step of purifying comprises binding the polypeptide of the present invention to a solid support. The term "solid support" refers to a matrix encompassing e.g. silica, crosslinked dextran, crosslinked polyacrylamide or crosslinked agarose and the like. Also included are in particular polypeptides, glass, polystyrene, polypropylene, polyethylene, polyethylene glycol (PEG), dextran, nylon, amylases, natural and modified celluloses, polyacrylamides, gabbros, and magnetite. A solid support is, in an aspect of the invention, a polysaccharide matrix selected from the group consisting of: sepharose, sephadex, agarose, sephacell, micro-cellulose, and alginate-beads. In another aspect, said solid support can consist of glass-beads, and/or polypeptide matrices.

In one aspect, the solid support is linked to the antibody of the present invention. The term "linked" means in one aspect stably linked or stably associated. In another aspect, linked includes interactions such as indirect or direct, non-reversible or reversible, physical and chemical, electrostatic, and/or covalent bonds. In an aspect, the antibody is covalently linked, either directly or via a linker molecule, to the solid support. The antibody may be bound to said solid support via a linker, including small molecular compounds and peptide (or polypeptide) linker molecules. The solid support can have virtually any possible structural configuration or arrangement as long as the coupled antibody is capable of binding to its antigen. Thus, the matrix or solid support may be spherical, as in a bead, or cylindrical, as in the inside surface of a test tube, or the external surface of a rod. Alternatively, the surface may be irregular or flat such as a sheet or test strip.

Said antibody linked to the solid support can be used e.g. in the manufacturing method of the present invention or in a diagnostic method. In one aspect, said manufacturing method may comprise a step of affinity chromatography, wherein said affinity chromatography is based on an antibody linked to a solid support. In one embodiment, said antibody is an antibody specifically binding to the proteolytically active polypeptide of the present invention. In another embodiment, said antibody is an antibody specifically binding to the proteolytically inactive polypeptide of the present invention.

In another aspect, the method for manufacturing the proteolytically active polypeptide of the present invention comprises purifying the polypeptide of the present invention from a mixture containing additional components. Purification may be based on e.g. polarity, electrical charge and size. Therefore, the method may in one aspect comprise one or more steps of separation selected from the group consisting of: normal-phase HPLC, reversed-phase HPLC, hydrophilic-interaction chromatography (HILIC), hydrophobic-interaction chromatography (HIC), ion-exchange chromatography (IEC) including anion-exchange chromatography and cation-exchange chromatography, size-exclusion chromatography (SEC), gel-permeation chromatography (GPC).

In another aspect, said purification comprises the steps of: (a) separation by anion exchange chromatography; (b) separation by size exclusion chromatography; (c) separation by hydrophobic interaction chromatography; and (d) separation by size exclusion chromatography.

One or more fractions collected from a chromatography column can be concentrated e.g. by precipitation or ultrafiltration.

In one aspect, the present invention relates to a composition comprising the proteolytically active polypeptide of the present invention. Using the method disclosed herein, it is possible to manufacture proteolytically active polypeptide of the present invention, which is substantially free of proteolytically inactive polypeptide. In other words, the present invention's method provides a proteolytically active polypeptide and a composition comprising no substantial contamination with inactive precursor protein of the polypeptide of the present invention. A composition is deemed to contain no substantial contamination or to be substantially free of proteolytically inactive precursor polypeptide if, by using a western blot based detection method, less than 5% of proteolytically inactive precursor can be detected, wherein said 5% refer to the amount of proteolytically inactive precursor in relation to the sum of proteolytically active and inactive polypeptide. In another aspect, said composition is substantially pure and comprises at least 50% proteolytically active polypeptide of the present invention, wherein said 50% refers to the amount of proteolytically active precursor in relation to the total amount of protein contained in the composition. In another aspect, said substantially pure composition comprises at least 75%, 80%, 90% or at least 98% proteolytically active polypeptide.

In another aspect, the present invention also relates to a polypeptide which is obtainable from the method for the manufacture of a proteolytically active polypeptide as described herein above and as illustrated in the Examples. Said proteolytically active polypeptide is in one aspect a proteolytically active polypeptide with the polypeptide sequence of SEQ ID NO: 1. In another aspect, the proteolytically active polypeptide is a polypeptide having at least 50% sequence identity with the sequence of SEQ ID NO: 1. In yet another aspect, the proteolytically active polypeptide is a polypeptide which comprises a polypeptide sequence having at least 50% sequence identity with the sequence of SEQ ID NO: 1. The term "polypeptide which is obtainable", as used herein refers in one aspect to a polypeptide that is translated from the nucleic acid of the present invention. The polypeptide can subsequently undergo posttranslational modification such as acylation, alkylation, amidation, amino acid addition, amino acid deletion, glycosylation, oxidation, S-glutathionylation, phosphorylation, sulphatation, proteolytic processing and the like. Moreover, the polypeptide may bind to a metal ion such as $Li^+$, $Na^+$, $K^+$, $Ag^+$, $Cs^+$, $Mg^{2+}$, $Ca^{2+}$, $Co^{2+}$, $Ni^{2+}$, $Mn^{2+}$, $Cu^{2+}$ or $Zn^{2+}$. Preferably, said metal ion is $Zn^{2+}$, $Mn^{2+}$ or $Co^{2+}$.

The present invention also relates in one aspect to an antibody specifically binding to the polypeptide of the present invention. The term "antibody" as used herein encompasses a monoclonal antibody, a polyclonal antibody, a single chain antibody, a human, humanized, primatized, or chimerized antibody, a bispecific antibody, a synthetic antibody, chemically or enzymatically modified derivatives, a fragment of any of said antibodies or aptamers consisting of naturally occurring and/or chemically modified nucleic acids. Fragments of said antibodies include F(ab')2, F(ab), Fv or scFv fragments or chemically or enzymatically modified derivatives of any of these fragments.

In one aspect, the antibody of the present invention shall specifically bind to the proteolytically active polypeptide of the present invention or its proteolytically inactive precursor. In one aspect, the antibody which is specific for the proteolytically active polypeptide of the present invention cross-reacts the proteolytically inactive polypeptide described herein. In another aspect, the antibody is capable of discriminating between the proteolytically active polypeptide of the present invention and its inactive precursor. In another aspect, the epitope for which said antibody is specific is located in an amino acid region that is present in the proteolytically inactive polypeptide but not in the proteolytically active polypeptide. For example, said epitope can be an epitope of a polypeptide region consisting of amino acid residues 1 to 248 of a polypeptide comprising the polypeptide sequence having at least 50% sequence identity with the sequence of SEQ ID NO: 2.

In another aspect, the epitope is formed by amino acid residues located N-terminal to amino acid 249 of a polypeptide comprising the polypeptide sequence having at least 50% sequence identity with the sequence of SEQ ID NO: 2. In another aspect, said epitope is removed from the proteolytically inactive polypeptide described herein by proteolytic processing.

In another aspect, the epitope for which the antibody of the present invention is specific is an epitope located at the N-terminus of a polypeptide comprising the polypeptide sequence having at least 50% sequence identity with the sequence of SEQ ID NO: 1. The term "N-terminus", as used in this aspect of the invention, refers to a region of the polypeptide comprising the N-terminal 50 amino acid residues of said polypeptide sequence, preferably the N-terminal 25 amino acid residues of said polypeptide sequence. In a particular aspect, the term refers to the N-terminal 14 amino acid residues. The term "epitope" as used herein relates to the antigenic determinant which is recognised by the antibody of the present invention. In one aspect, the epitope is a linear epitope, in another aspect the epitope is a conformational epitope. In a particular aspect, the antigenic determinant consists of a peptide having the amino acid sequence of the N-terminus of the proteolytically active polypeptide of the present invention, wherein said peptide can have an amino acid length of 7 to 14, preferably of 8, 9, 10, 11, 12, 13 or 14 amino acid residues.

The term "specifically binds" or "specifically binding to" in one aspect means that the antibody of the present invention does not cross-react to a significant extent with other epitopes either on the polypeptide of the present invention or on other polypeptides in general. Epitope specificity is an important characteristic of the antibody of the present invention. Specificity of the antibody with respect to the proteolytically active versus proteolytically inactive polypeptide shall be, in an aspect, at least 95%, at least 96%, at least 97%, at least 98%, at least 99%. Specific binding can be tested by various well known techniques including, e.g., competition studies. Another important characteristic is the sensitivity of the antibody. Sensitivity shall be, in one aspect of the invention, such that at least 70%, at least 80%, at least 90%, at least 95% of the epitope comprised by a sample is bound. Sensitivity can be tested by well known techniques. Those skilled in the art will be able to determine operative and optimal assay conditions for each determination by employing routine experimentation. Conventional techniques for binding studies include radioimmunoassay, ELISA, equilibrium dialysis, isothermal microcalorimetry, BIACORE® assays (surface plasmon reasonance, SPR) or other surface adsorption methods. The BIACORE® SPR system measures the antibody-antigen interaction. SPR response reflects a change in mass concentration at the detector surface as analytes bind or dissociate. Based on SPR, real-time BIACORE® measurements monitor interactions directly as they occur, see BIAapplications Handbook, version AB (reprinted 1998), BIACORE® code No: BR-1001-86; BIAtechnology Handbook, version AB (reprinted 1998), BIACORE® code No: BR-1001-84. The binding properties such as sensitivity of an antibody of the present invention may, in principle, be determined by binding studies using an immobilised antigen (the ligand) presented on a sensor surface. The antibody to be tested (the analyte) will be provided in the mobile phase, i.e. in a solution. In some cases, the antigen is attached indirectly to the surface through binding to another immobilised molecule which is referred as the capturing molecule. When the antibody is injected in a discrete pulse across the surface with the immobilised antigens, essentially three phases can be subdivided: (i) Association of antibody with the antigen during sample injection; (ii) Equilibrium or steady state during sample injection, where the rate of antibody binding is balanced by dissociation from the antibody-antigen complex; (iii) Dissociation of antibody from the surface during buffer flow. It will be understood that such an assay can alternatively be performed with immobilised antibodies to be investigated and an antigen containing solution as the mobile phase. The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$). In an aspect of the invention, the antibody of the present invention has a $K_D$ of less than 0.5 µM, in another aspect less than 0.05 µM and, in another aspect, less than 0.02 µM.

The antibody as referred to in the present invention can be manufactured by using methods which are described, e.g., in Harlow and Lane, 1988 (Harlow and Lane, "Antibodies, A Laboratory Manual", CSH Press, Cold Spring Harbor, 1988). Monoclonal antibodies can be prepared by the techniques originally described in Kohler & Milstein, 1975 (Kohler & Milstein 1975, Nature 256: 495) and Galfre & Milstein, 1981 (Galfre & Milstein 1981, Meth Enzymol 73: 3). Said techniques comprise the fusion of mouse myeloma cells to spleen cells derived from immunized mammals. Antibodies can be further improved by techniques well known in the art. For example, surface plasmon resonance as employed in the BIACORE® system can be used to increase the efficiency of phage antibodies which bind to the aforementioned epitope within polypeptide of the present invention (cf. Schier et al., 1996, Human Antibodies Hybridomas 7: 97; Malmborg et al., 1995, J. Immunol Methods 183: 7).

In an aspect of the invention, the antibody is produced by using a peptide comprising or consisting of the aforementioned epitope. The peptide can be produced e.g. synthetically or by recombinant expression. Alternatively, the antibody of the invention can be produced by applying natural occurring proteolytically active or inactive polypeptide of the present invention. In the latter case, it is to be understood that the resulting antibodies shall be further tested for specificity with respect to the polypeptide of the present invention. In a further aspect of the invention, a monoclonal antibody of the invention is produced by using a polypeptide of the present invention which can be treated by a detergent in order to make the epitope immunologically available. However, it will be understood that in a case were the antibody shall be directed against a conformational epitope, no such detergent treatment shall be carried out. In a further aspect, immune-stimulation agents such as keyhole limpet hemocyanin (KLH) may be also applied in such process, especially when using a synthetic peptide.

The antibody of the present invention can be used, for example, for affinity chromatography, immunoprecipitation, and immunolocalization of the polypeptide of the present invention as well as for the monitoring of the presence of said polypeptide in samples or in recombinant organisms. Moreover, the antibody of the present invention may be used in a detection method or in a diagnostic method. In a particular aspect, the antibody of the present invention is used in Western Blot or ELISA. In addition, the antibody of the present invention can be used in therapeutic applications. In particular, the antibody can be used for inhibiting the activity of the proteolytically active polypeptide of the present invention. Therefore, the antibody of the present invention also has various therapeutic applications described herein below.

The present invention also relates to the use of the proteolytically active polypeptide of the present invention in a method for proteolytically processing a polypeptide. In one aspect, the present invention relates to a method for the manufacture of a proteolytically processed polypeptide, comprising the step of contacting: (a) a first polypeptide, said first polypeptide being the polypeptide of the present invention, with (b) a second polypeptide, said second polypeptide being susceptible to proteolysis by said first polypeptide, wherein said contacting results in proteolytic processing of said second polypeptide into at least two cleavage products.

The present invention also relates to the use of Lys-N and/or Lys-C and/or arginyl endopeptidase (endoproteinase Arg-C, LeR) from *Lysobacter enzymogenes* (ATCC 29487) (Wright D S, Graham L D, Jennings P A. Biochim Biophys Acta. 1998 Dec. 22; 1443(3):369-74). Moreover, also encompassed is the use of plasmin and/or omptin (OmpT), a membrane-bound serine protease that cleaves at (Arg/Lys)-(Arg/Lys) motifs (K. Sugimura and T. Nishihara. J. Bacteriol. 170 (1988), pp. 5625-5632) in a method for proteolytically processing CNT such as BoNT/A. In one aspect, the present invention relates to a method for the manufacture of a proteolytically processed polypeptide, comprising the step of contacting: (a) a first polypeptide, said first polypeptide being Lys-C or Lys-N, with (b) a second polypeptide, said second polypeptide being susceptible to proteolysis by said first polypeptide, wherein said contacting results in proteolytic processing of said second polypeptide into at least two cleavage products, and wherein the second polypeptide is the single chain of BoNT/A. The term "Lys-C" refers to the 33 kDa serine endoproteinase Lys-C from Lysobacter enzymogenes (Lysyl endopeptidase, LeK, Genbank acc. Q7M135) that specifically cleaves peptide bonds C-terminally to lysine or a homolog thereof having at least 60% sequence identity. The term "Lys-N" refers to the metalloendopeptidase Lys-N isolated from *Grifola frondosa* and *Pleurotus ostreatus* (Nonaka T et al., 1997, J Biol Chem. 272:30032-30039; Nonaka T et al., 1998, J Biochem. 1998 124:157-162; Hori T et al., 2001, Acta Crystallogr D Biol Crystallogr. 57:361-368). Also encompassed by the term are homologs of said protease having at least 60% sequence identity.

This method can be used, for example, for manufacturing proteolytically processed neurotoxin (CNT) or botulinum neurotoxin (BoNT). The term "BoNT", as used throughout this invention, means botulinum neurotoxin and refers to neurotoxin obtainable from *C. botulinum* such as BoNT of serotype A, B, C1, D, E, F or G. Also encompassed by the term "CNT" and "BoNT" is recombinant and modified neurotoxin comprising one or more modifications including chemical modification or genetic modification. The term "genetic modification" means deletion, substitution or addition of one or more amino acid residues. Using the method of the present invention, it is now possible to obtain neurotoxin compositions with significantly less contamination by unprocessed or partially processed neurotoxin, since those contaminants are efficiently processed into di-chain neurotoxin. In one aspect, the di-chain neurotoxin is a native di-chain neurotoxin, wherein the C-terminus of the light chain and the N-terminus of the heavy chain are identical to the corresponding fully processed di-chain neurotoxin isolated from wildtype clostridia.

The term "contacting" as used herein refers to bringing at least two different compounds in physical proximity as to allow physical and/or chemical interaction of said compounds. In accordance with the method of this invention, the said two different compounds are, in an aspect, the first and the second polypeptide which are comprised by the solution. Contacting is carried out under conditions and for a time being sufficient to allow interaction of the first and second polypeptide. The term "proteolytically processed polypeptide" as used herein refers in one aspect to a polypeptide, the polypeptide chain of which has been hydrolysed or cleaved at one or more peptide bonds. In another aspect, the term refers to a polypeptide that has been proteolytically cleaved by an endoproteinase or endopeptidase. In another aspect, the term refers to a polypeptide which has been cleaved to a degree of at least 50%. In another aspect, said proteolytically processed polypeptide is the second polypeptide. In another aspect, at least 60%, 70%, 80%, 90% or 95% are proteolytically processed.

The term "first polypeptide", as used herein, refers to the polypeptide of the present invention, i.e. the proteolytically active or activated polypeptide, also designated "active BoNTHydrolase". Since the active BoNTHydrolase can be obtained from the supernatant of *C. botulinum*, it was initially termed native BoNTHydrolase, abbreviated "nBH". However, the term "first polypeptide" and "nBH" also refers to BoNTHydrolases that are obtainable from other sources. The term "second polypeptide", as used herein, refers to the substrate of said first polypeptide. The term "being susceptible to proteolysis" refers to a feature or requirement of the second polypeptide and is used herein meaning that the second polypeptide is proteolytically cleavable by said first polypeptide. In other words, the term "being susceptible to proteolysis" means that the second polypeptide comprises a protease recognition and cleavage site allowing it to function as a substrate of the first polypeptide. The "second polypeptide" is a substrate of the first polypeptide and is proteolytically processed into two or more cleavage products. Using the assay described herein above, the skilled person can test whether a given polypeptide is a substrate of the first polypeptide and, thus, a "second polypeptide" according to present invention's definition. The term "at least two cleavage products" includes, for example, up to two, three, four, five and up to six cleavage products.

This method can be used, for example, for preparing a pharmaceutical composition comprising clostridial neurotoxin or for generating polypeptide fragments used in a method of mass spectrometry. The first polypeptide and the second polypeptide can be contacted at various steps in the manufacturing process of proteolytically processed polypeptide. In one aspect, the step of contacting the first polypeptide and the second polypeptide is within a cell. In a particular aspect of this embodiment, the first and the second polypeptide are expressed in said cell.

In another aspect, said step of contacting is in a cell lysate or in a purified cell lysate. This aspect encompasses adding the first polypeptide to the lysate or the purified lysate. The first polypeptide can be added at various steps during purification of the second polypeptide from the cell lysate. For example, the first polypeptide can be added prior to or after: protein precipitation, ion exchange chromatography, hydrophobic interaction chromatography and/or size exclusion chromatography. Moreover, also encompassed is the addition of the first polypeptide to a pharmaceutical composition. In this aspect, the polypeptide of the present invention is used e.g. for proteolytically cleaving the second polypeptide e.g. for activating a second polypeptide which is a therapeutic agent contained in the pharmaceutical composition. Also envisaged is the administration of the first polypeptide to a subject, in order to proteolytically process a second polypeptide in the subject. Administration also includes co-administration of the first and the second polypeptide. Also encompassed by this method is a step of incubation at conditions and for a time sufficient to cleave the second polypeptide. In one aspect, the conditions can comprise adding a buffer selected from the group consisting of 100 mM Tris-HCl, pH 8.0 or PBS (50 mM $Na_2HPO_4$, 150 mM NaCl, pH 7.4). Preferred buffer conditions include 100 mM Tris-HCl, pH 8.0. The "time sufficient to cleave" can be determined using the assay described herein above. In one aspect, said "time sufficient to cleave" depends on the degree of cleavage that the proteolytically processed polypeptide or a composition comprising it should have. In one aspect, the method comprises a step of incubating the first and the second polypeptide for at least 30 min, 60 min, 120 min or at least 240 min. In another aspect, the first and second polypeptide are incubated for up to 30 min, 60 min, 120 min, 240 min, 480 min or up to 600 min. In another aspect, the method comprises a step of incubating the first and the second polypeptide at 4° C. or at 37° C. In another aspect, the method comprises a step of incubating for up to 1 h, up to 2 h, 4 h, 6 h, 10 h or up to 16 h.

In one aspect, the polypeptide chain of said second polypeptide comprises a sequence selected from any one of SEQ ID NOs: 4 to 25. In a more particular aspect, the polypeptide chain of said second polypeptide comprises a sequence selected from any one of SEQ ID NOs: 4 to 25 and wherein the second polypeptide is cleaved C-terminal to a basic amino acid residue within said sequence of any one of SEQ ID NOs: 4 to 25. Said sequences represent amino acid sequences of known substrates of the proteolytically active polypeptide of the present invention. As shown herein, said substrates are cleaved C-terminal to a basic amino acid residue contained in the sequence, compare Table 1, column LC and HN. In a preferred aspect, said second polypeptide comprises a sequence selected from SEQ ID NO: 4 to 10. In another preferred aspect, said second polypeptide is BoNT/A or a derivative thereof, including e.g. the polypeptide of SEQ ID NO: 3 and derivatives thereof. The term "derivative" as used with respect to this and other aspects of the invention, comprises amino acid mutations such as addition, substitution, deletion or truncation of one or more amino acid residues.

In one aspect, the second polypeptide comprises a derivative of any one of SEQ ID NOs: 4 to 25, or of SEQ ID NO: 3, wherein said derivative has one or more point mutation and/or one or more additional amino acid residues. In another aspect, said derivative has up to 1, up to 2, up to 3, up to 4, up to 5, up to 6, up to 7, up to 8, up to 9, up to 10, up to 15 point mutations. By using the activity assay for determining protease activity, as described herein, the skilled person can determine whether a given derivative is processed by the proteolytically active polypeptide of the present invention. In another aspect, the derivative contains a point mutation changing a basic amino acid residue into a non-basic amino acid residue. In another aspect, the derivative has at least 50% sequence identity with any one of SEQ ID NOs: 4 to 25. In another aspect, said derivative or a polypeptide comprising the derivative is a substrate of the first polypeptide and is proteolytically cleavable by the first polypeptide. A typical example is a derivative of SEQ ID NO: 3 comprising e.g. one or more point mutations in the light or heavy chain.

In another aspect, said second polypeptide comprises (a) a polypeptide sequence having at least 30% sequence identity with the sequence of SEQ ID NO: 3 [(BoNT/A of ATCC 3502, Genbank acc. AAA23262)]; or (b) a polypeptide sequence selected from the group consisting of Tetanus neurotoxin, protein of the coagulation cascade Factor X or Prothrombin (Factor II), digestive enzymes of the pancreas like trypsin, chymotrypsin, pepsin, papain. At least 30% means at least 30%, at least 40%, at least 50%, at least 85%. In a particular aspect, the sequence identity of said second polypeptide sequence having at least 50% sequence identity with the sequence of SEQ ID NO: 3 is determined based on amino acid position 420 to 466 of SEQ ID NO: 3, in another aspect, said sequence identity is determined based on any one of SEQ ID NOs: 4 to 25. In other words, said aspect refers to a second polypeptide which comprises a polypeptide sequence which has e.g. at least 30% sequence identity to the polypeptide sequence found between amino acid positions 420 to 466 of SEQ ID NO: 3 or at least 30% sequence identity to the polypeptide sequence of any one of SEQ ID NOs: 4 to 25. A polypeptide according to this definition is, e.g. obtainable from *C. botulinum, C. tetani* or *C. sporogenes*. Said second polypeptide may be, for example, a naturally occurring neurotoxin such as BoNT/A, B, C1, D, E, F or G or a derivative thereof comprising one or more amino acid mutations such as addition, substitution, deletion or truncation of one or more amino acid residues. Encompassed are e.g. derivatives lacking e.g. the native neurotoxin $H_C$ domain or parts thereof or derivatives with other amino acid residues replacing the neurotoxin $H_C$ domain as well as derivatives with an additional light chain or another proteinaceous cargo molecule fused N-terminally to the light chain of BoNT.

In another aspect, the second polypeptide may contain additional amino acid residues at the N- or C-terminus or at an internal position. The additional amino acid residues may be flanked by one or more protease cleavage sites. In another aspect, the additional amino acid sequence functions as a detectable tag and/or allows binding to a solid support. An example is a his tag or a GST tag. Another example is the amino acid sequence VPPTPGSAWSHPQFEK containing the Streptag, preferably added to the C-terminus.

In a particular aspect, said second polypeptide is a polypeptide comprising a polypeptide sequence as shown in GenBank no: CBZ04958.1, YP_002805603.1, ZP_02994746.1, YP_001788403.1, YP_001782718.1, ZP_02616437.1, ZP_02614241.1, YP_001392361.1, YP_001255575.1 or a homolog thereof having at least 50% sequence identity.

In another aspect, the biological activity of said second polypeptide is modulated by the proteolytic cleavage. It is well known to the skilled person, that the function of many polypeptides can be modulated by proteolytic processing. "Modulated" as used herein means increased or decreased, activated or inactivated. For example, the biological activity of many clostridial neurotoxins is increased or triggered by proteolytically processing a single chain neurotoxin into a di-chain neurotoxin, wherein the di-chain neurotoxin is composed of a light and a heavy polypeptide chain, which are covalently linked through a disulfide-bridge. The biological activity of the neurotoxin encompasses at least three separate activities: the first activity is a "proteolytic activity" residing in the light chain of the neurotoxin and is responsible for hydrolysing the peptide bond of one or more polypeptides involved in the regulation of cellular membrane fusion. A second activity is a "translocation activity", residing at the N-terminal end of the heavy chain of the processed neurotoxin and is involved in the transport of the light chain across the lysosomal membrane and into the cytoplasm. A third activity is a "receptor binding activity", residing at the C-terminal end of the heavy chain of the processed neurotoxin and involved in binding and uptake of the neurotoxin to a target cell. In a preferred aspect, the term biological activity as used herein means proteolytic activity. In a more preferred aspect, the term means increased proteolytic activity.

Biological activity of clostridial neurotoxin can be measured by various tests, all of which are known to the person skilled in the art. These tests allow determining one or more of the activities mentioned above. For example, the mouse $LD_{50}$ assay or the ex vivo mouse phrenic nerve hemidiaphragm (MPN) assay as described by Pearce et al., 1994 (Pearce L B, Borodic G E, First E R, MacCallum R D (1994), Toxicol Appl Pharmacol 128: 69-77) and Habermann et al., 1980 (Habermann E, Dreyer F, Bigalke H. (1980), Naunyn Schmiedebergs Arch Pharmacol. 311:33-40) allow determining the toxic effect of a given neurotoxin preparation on a living organism or an isolated neuromuscular preparation. For establishing the toxic effect in an $LD_{50}$ assay, the neurotoxin must be biologically active in each of said three activities mentioned above. Moreover, various other assays are available, allowing e.g. to determine whether a neurotoxin or the light chain of the neurotoxin is proteolytically active. Such assays are e.g. based on contacting BoNT/A with SNAP-25. Alternatively, a peptide representing the cleavage site of SNAP-25 can be used, wherein the peptide can be labelled to ease detection. In a preferred aspect, biological activity is determined by using the MPN assay described herein above.

In another aspect, said first polypeptide is activated by proteolytically processing an inactive precursor polypeptide, said inactive precursor polypeptide comprising a polypeptide sequence having at least 60% sequence identity with the sequence of SEQ ID NO: 2. This aspect rests on the observation that a polypeptide having the polypeptide sequence of SEQ ID NO: 2 is proteolytically inactive, while N-terminal truncations thereof are proteolytically active. It is also envisaged by the present invention to use the proteolytically inactive polypeptide in the methods described herein. The proteolytically inactive polypeptide described herein can be activated e.g. by removing a fragment from the N-terminus or the entire N-terminus comprising amino acid residues 1 to 248 of SEQ ID NO: 2. In one aspect, the N-terminus is removed by a protease, in another aspect, the N-terminus is removed by autoproteolysis of SEQ ID NO: 2. 60% sequence identity refers to a sequence alignment with full length NT02CB1447.

In another aspect, the present invention's method for the manufacture of a proteolytically processed polypeptide comprises the step of purifying the proteolytically processed second polypeptide or at least one or two or more cleavage products thereof. Purification of C. botulinum expressed BoNT/A may be done e.g. as essentially described in the prior art (DasGupta 1984, Toxicon 22, 415; Sathyamoorthy 1985, J Biol Chemistry 260, 10461). In particular, purification of the neurotoxin can contain one or more precipitation- and extraction steps, one or more concentration steps, and further distinct chromatographic steps. Recombinant single chain BoNT/A and its purification is described in prior art (Rummel et al., 2004, Mol Microbiol. 51:631-43).

In a preferred embodiment, the Clostridium strain is C. botulinum, for example producing BoNT/A, or a derivative thereof. For fermentation, the process described by DasGupta B. R. et al. in Toxicon, vol. 22, No. 3, p. 414 to 424, 1984, can be used. Therefore 0.5% yeast extract and 0.6% autoclaved yeast paste is added to 2% of the N-Z-amine type A medium, and a pH of 7.2 will be adjusted with the help of 4N NaOH, and the medium prepared in such a way will afterwards be autoclaved. To this medium separately autoclaved glucose (20% by weight per volume) may be added, to come to a final concentration of glucose of 0.5% in the medium. Incubation may occur e.g. at 37° C. without stirring, wherein the fermentation is discontinued e.g. after 96 hours. It is within the scope of the present invention that besides the batch fermentation described before also semi-batch fermentation, repeated batch fermentation or continuous fermentation can be performed.

After the actual fermentation and separation of the fermentation medium from the cells the fermentation medium may undergo a first precipitation with the goal of removing large proteins. The precipitation is preferably an acid precipitation. Reaction conditions for such an acid precipitation are known to those skilled in the art. Typically 1.5 M $H_2SO_4$ may be used, to acidify the supernatant to a pH of 3.5. The centrifugation usually occurs for 20 minutes at 2400×g at 4° C. The pellet received through centrifugation may be washed with water, preferably repeatedly. Subsequently, the pellet may be extracted with a 0.1 M citric acid-trisodium citrate buffer, pH 5.5 e.g. for an hour. Subsequently, a further centrifugation step may be performed, e.g. at 9800×g for 20 minutes at 4° C. The so obtained pellet optionally can then again be extracted as described before. The supernatant of the extraction, and both supernatants in case of repetition of the extraction, may then be subjected to protamine sulphate precipitation. The precipitation may continue overnight, e.g. at 8° C. Subsequently, the precipitate may be centrifuged, e.g. for 20 minutes at 4° C. and at 12,000×g. The supernatant of centrifugation may be subject to a precipitation such as an ammonium sulphate precipitation, whereby other larger proteins can be removed. After the ammonium sulphate precipitation step another centrifugation step may be added and subsequently the so obtained pellet may be redissolved and, optionally, be subjected to a dialysis. The extract which is preferably dialysed and centrifuged again, can be subjected to a succession of chromatography steps with the objective of purifying the neurotoxin. Each of the chromatography steps serves to remove contaminants such as protamine sulphate, remaining DNA, parts of smaller proteins and middle-sized proteins as well as the hemagglutinins of the botulinum neurotoxin protein complex. For this purpose, one or more chromatography steps may be used in a preferred embodiment. Optionally, the eluate of, e.g. the last chromatography step, may be filtrated in order to reduce germs. Optionally the eluate can be diluted before filtration and suitable adjuvants can be added. During further steps another sterile filtration may be carried out after addition of the adjuvants. In one aspect, the filtration is carried out in reaction containers which may then be subject to a step of lyophilization.

The present invention also relates to a composition obtainable by the present invention's method for the manufacture of a proteolytically processed polypeptide. In one aspect, said composition comprises a mixture of processed and unprocessed second polypeptide, wherein said mixture may contain less than 5%, 4%, 3%, 2% or less than 1% unprocessed second polypeptide. In an aspect of said composition, said second polypeptide is BoNT or a derivative thereof. The BoNT can e.g. be selected from group consisting of BoNT of serotype A, B, C, D, E, F and G, including a derivative thereof. The composition can be e.g. a liquid or a solid composition and may contain one or more carrier, adjuvants and/or excipients.

In another aspect, the present invention also relates to a method for the manufacture of a medicament, i.e. a pharmaceutical composition, comprising the steps of the aforementioned method and the further step of formulating the purified di-chain neurotoxin as medicament. In one aspect, said medicament comprises a mixture of processed and unprocessed second polypeptide, wherein said mixture contains less than 5% unprocessed second polypeptide. In preferred embodiments, the mixture contains less than 4%, 3%, 2% or less than 1% unprocessed second polypeptide.

The present invention also relates to various medical uses of the compounds disclosed herein:

In one aspect, the present invention relates to a proteolytically active polypeptide according to the present invention for use as a medicament or in a pharmaceutical composition.

In another aspect, the present invention relates to a composition according to the present invention for use as a medicament or in pharmaceutical composition.

In yet another aspect, the present invention relates to an antibody according to the present invention for use as a medicament or in pharmaceutical composition.

In yet another aspect, the present invention relates to an inhibitor according to the present invention for use as a medicament or in pharmaceutical composition.

In particular, the present invention relates to a pharmaceutical composition comprising the polypeptide of the present invention, the antibody of the present invention, the composition of the present invention or the inhibitor of the present invention.

The term "composition" as used herein refers to any composition formulated in solid, liquid, aerosol (or gaseous) form and the like. Said composition comprises e.g. a therapeutically active compound of the invention optionally together with suitable auxiliary compounds such as diluents or carriers or further ingredients. In one aspect, the therapeutically active compound is the proteolytically active polypeptide of the present invention. In another aspect, the therapeutic compound is the proteolytically processed second polypeptide as described herein above such as the di-chain neurotoxin. In another aspect, the therapeutically active compound is the antibody of the present invention. In another aspect, the therapeutically active compound is the inhibitor of the proteolytically active polypeptide of the present invention.

In this context, it is distinguished for the present invention between auxiliary compounds, i.e. compounds which do not contribute to the effects elicited by the compound of the present invention upon application of the composition for its desired purpose, and further ingredients, i.e. compounds which contribute a further effect or modulate the effect of the compound of the present invention. Suitable diluents and/or carriers depend on the purpose for which the composition is to be used and the other ingredients. The person skilled in the art can determine such suitable diluents and/or carriers without further ado.

The carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatine, agar, pectin, acacia, magnesium stearate, stearic acid and the like. Exemplary of liquid carriers are phosphate buffered saline solution, syrup, oil, water, emulsions, various types of wetting agents, and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the combination. Examples of such diluents are distilled water, physiological saline, Ringer's solutions, dextrose solution, and Hank's solution, in addition, the pharmaceutical composition or formulation may also include other carriers, adjuvants, or non-toxic, non-therapeutic, non-immunogenic stabilisers and the like.

In one aspect, a pharmaceutical composition as used herein comprises the biologically active neurotoxin obtained by the method of the present invention, optionally, one or more pharmaceutically acceptable carrier. The active neurotoxin can be present in liquid or lyophilized form. In an aspect, said compound can be present together with glycerol, protein stabilisers (e.g., human serum albumin (HSA)) or non-proteinaceous stabilisers such as polyvinylpyrrolidone or hyaluronic acid. The pharmaceutical composition is, in one aspect, administered topically. Conventionally used drug administration is administered intra-muscular, subcutaneous (near glands). However, depending on the nature and the mode of action of a compound the pharmaceutical composition may be administered by other routes as well.

The di-chain neurotoxin polypeptide is the active ingredient of the composition, and is in one aspect administered in conventional dosage forms prepared by combining the drug with standard pharmaceutical carriers according to conventional procedures. These procedures may involve mixing, granulating, and compression, or dissolving the ingredients as appropriate to the desired preparation. It will be appreciated that the form and character of the pharmaceutical acceptable carrier or diluent is dictated by the amount of active ingredient with which it is to be combined, the route of administration, and other well-known variables.

A therapeutically effective dose refers to an amount of the compound, the neurotoxin, to be used in a pharmaceutical composition of the present invention which prevents, ameliorates or treats the symptoms accompanying a disease or condition referred to in this specification. Therapeutic efficacy and toxicity of the compound can be determined by standard pharmaceutical procedures in cell cultures or experimental animals, e.g., ED50 (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$.

The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. The pharmaceutical compositions and formulations referred to herein are administered at least once in order to treat or ameliorate or prevent a disease or condition recited in this specification. However, the said pharmaceutical compositions may be administered more than one time.

In a further aspect of the invention, the aforementioned composition is a medicament or a cosmetic composition. In one aspect the said medicament comprising the biologically active neurotoxin can be used for prevention and/or treatment of at least one of the following diseases and disorders: voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, in a further aspect also blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramp, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitant mutational dysphoria, upper oesophageal sphincter dysfunction, vocal fold granuloma, stuttering Gilles de la Tourette syndrome, middle ear myoclonus, protective larynx closure, postlaryngectomy, speech failure, protective ptosis, entropion sphincter Odii dysfunction, pseudoachalasia, non-achalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, cosmetic use craw's feet, frowning facial asymmetries, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinson's, in amyotrophic lateral sclerosis spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, migraine, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, myelon tumors, snoring (WO 2000/033863). For details and symptoms see, e.g., Jost 2007, Drugs 67(5), 669 or Dressler 2000 in Botulinum Toxin Therapy, Thieme Verlag, Stuttgart, New York.

In another aspect of the invention, the composition is a cosmetic composition which can be formulated as described for a pharmaceutical composition above. For a cosmetic composition, likewise, it is envisaged that the compound of the present invention is in an aspect used in substantially pure form. Cosmetic compositions are, in a further aspect, to be applied intramuscular. In an even further aspect of the invention, cosmetic compositions comprising the neurotoxin can be formulated as an anti-wrinkle solution.

In another aspect, the pharmaceutical composition comprises the antibody or the inhibitor of the present invention. Since the present invention's polypeptide is responsible for activating clostridial neurotoxins, the antibody will be useful for reducing the toxic effect observed during infection with clostridia. Therefore, the antibody of the present invention can in one aspect be used for treating an infection by Clostridia, including *Clostridium perfringens, Clostridium difficile, Clostridium tetani, Clostridium botulinum, Clostridium baratii, Clostridium butyricum, Clostridium sporogenes, Clostridium acetobutylicum, Clostridium haemolyticum, Clostridium nogi* and *Clostridium oedematiens*. Furthermore, the antibody of the present invention can in another aspect be used for the treatment of symptoms associated with said infection. Moreover, said antibody can be used in the treatment of a condition or a symptom associated with the condition, wherein the condition is selected from Botulism, Tetanus, Pseudomembranous colitis, Gangrene, Food poisoning and the like.

In another aspect, the pharmaceutical composition comprises the proteolytically active polypeptide of the present invention. Said pharmaceutical composition can be used in one aspect for proteolytically cleaving polypeptides involved in coaglutination, in particular for treating patients with hypocoaglutination. In another aspect, the pharmaceutical composition can be used as fibrinolyticum, in particular for treating patients with myocard infarct, pulmonary embolism, deep venous thromboembolism, i.e. for removing blood clots. Also envisaged is the use of the pharmaceutical composition in the treatment of stroke. Moreover, in other aspects, the pharmaceutical composition can be used in the treatment of exokrine pancreatic insufficiency for replacing either of trypsin, chemotrypsin, pepsin. Moreover, in other aspects, the pharmaceutical composition can be used in the treatment of patients affected by inflammatory reactions, in the treatment of cancer patients, in particular for proteolytically cleaving surface exposed tumor antigens. Moreover, in another aspect, the pharmaceutical composition can be used in the treatment of papilloma.

The present invention also relates to a method of screening for an inhibitor comprising the step of (a) contacting the proteolytically active polypeptide of the present invention with a known substrate and, optionally, with a putative inhibitor; and (b) determining the effect of the putative inhibitor on the conversion of substrate into cleavage product, wherein a reduction in the amount of cleavage product is indicative for the inhibitory effect of the putative inhibitor. In one aspect the putative inhibitor is a peptide comprising an amino acid sequence selected from any one of SEQ ID NOs: 4 to 25, wherein at least one basic amino acid of said amino acid sequence is replaced with a non-basic amino acid. In a further aspect, said peptide comprises one or more chemical modifications. In another aspect, the inhibitor is a peptidomimetic of said peptide. In another aspect, the putative inhibitor is part of a chemical compound microarray, i.e. a collection of organic chemical compounds. In yet another aspect, the inhibitor is the antibody of the present invention. This method is useful for identifying compounds capable of inhibiting the proteolytically active polypeptide of the present invention. An initial screen may be based on, for example, a peptide comprising an amino acid sequence selected from any one of SEQ ID NOs: 4 to 25. Peptides capable of inhibiting the polypeptide of the present invention may be modified in order to increase inhibition. Modifications include amino acid substitution or chemical modifications. Typically, this method is carried out by contacting the polypeptide of the present invention with a known substrate in the presence and absence of a putative inhibitor (step (a) of the method) and by comparing the effect of the putative inhibitor on the conversion of substrate into cleavage product. A reduction of the conversion rate in the presence of putative inhibitor is indicative of an inhibitory effect.

The present invention also relates to an inhibitor of the proteolytically active polypeptide of the present invention, wherein said inhibitor is (a) an inhibitor comprising an amino acid sequence as shown in any one of SEQ ID NOs: 4 to 25, wherein a basic amino acid contained therein is replaced with a non-basic amino acid; or (b) the antibody of the present invention.

All references cited in this specification are herewith incorporated by reference with respect to their entire disclosure content and the disclosure content specifically mentioned in this specification.

The Sequence Listing Shows:

SEQ ID NO: 1: proteolytically active polypeptide derived from a *Clostridium botulinum* strain ATCC 3502, GenBank accession No: "CAL82988.1", lacking 248 N-terminal amino acid residues SEQ ID NO: 2: proteolytically inactive polypeptide derived from a *Clostridium botulinum* strain ATCC 3502, GenBank accession No: "CAL82988.1"

SEQ ID NO: 3: BoNT/A of ATCC 3502, Genbank acc. "AAA23262"

SEQ ID NO: 4: Loop of BoNT/A1
SEQ ID NO: 5: Loop of BoNT/A2/A6
SEQ ID NO: 6: Loop of BoNT/A3
SEQ ID NO: 7: Loop of BoNT/A3
SEQ ID NO: 8: Loop of BoNT/A4
SEQ ID NO: 9: Loop of BoNT/A5
SEQ ID NO: 10: Loop of BoNT/A7
SEQ ID NO: 11: Loop of BoNT/B1/B4bv/B6
SEQ ID NO: 12: Loop of BoNT/B2/B3
SEQ ID NO: 13: Loop of BoNT/B5np
SEQ ID NO: 14: Loop of BoNT/C/CD
SEQ ID NO: 15: Loop of BoNT/D
SEQ ID NO: 16: Loop of BoNT/DC
SEQ ID NO: 17: Loop of BoNT/E1-E5
SEQ ID NO: 18: Loop of BoNT/E6
SEQ ID NO: 19: Loop of BoNT/F1/F6
SEQ ID NO: 20: Loop of BoNT/F2/F3
SEQ ID NO: 21: Loop of BoNT/F4
SEQ ID NO: 22: Loop of BoNT/F5
SEQ ID NO: 23: Loop of BoNT/F7
SEQ ID NO: 24: Loop of BoNT/G
SEQ ID NO: 25: Loop of TeNT
SEQ ID NO: 26: nucleic acid sequence encoding SEQ ID NO: 1
SEQ ID NO: 27: nucleic acid sequence encoding SEQ ID NO: 2

The following Examples illustrate the invention and shall, whatsoever, not be construed to limit its scope.

EXAMPLES

Example 1

Purification and Characterisation of the Native BoNTHydrolase (nBH), Which Specifically Cleaves Single Chain BoNT/A into its Active di-Chain Form (1) Read-out system/activity test: To specifically detect and purify an enzymatic activity hydrolysing botulinum neurotoxin A (BoNT/A) into the 50 kDa light chain (LC) and 100 kDa heavy chain (HC) in culture supernatants of *C. botulinum* and in between chromatographic steps we expressed the 150 kDa BoNT/A as single chain (sc) polypeptide in *E. coli*. Incubation of the recombinant scBoNT/A with the appropriate enzymatic activity (nBH) should yield a 50 kDa LC and a 100 kDa HC visualised by reducing 10-13% SDS-PAGE.

(2) Clostridial protease expression: A single colony of *C. botulinum* strain ATCC 3502 was inoculated in 100 ml brain heart infusion (BHI) media and the culture was incubated over night at 37° C. under anaerobic conditions. 10 ml of O/N culture was inoculated into 1 l BHI media and anaerobically incubated for 48-72 h.

(3) Ammonium sulphate precipitation: The 1 l culture supernatant was harvested by centrifugation (4° C., 6500×g, 25 min). Ammonium sulphate was added to a final concentration of 85% (here 575 g), the suspension was stirred for 6 hours at 4° C. and subsequently centrifuged (4° C., 6500×g, 30 min). The pelleted ammonium sulphate precipitate was dissolved in a small volume (here 5 ml) of 50 mM NaP pH 7.5 and dialysed against 50 mM NaP, 150 mM NaCl pH 7.5. Finally, the dialysate was centrifuged (4° C., 40000×g, 60 min) and the supernatant used for the IEC.

(4) Ion exchange chromatography (IEC, column HiPrep 16/10 Q FF): Supernatant of (3) (FIG. 1, lane 3) was applied to a HiPrep 16/10 Q FF anion-exchange column equilibrated and run with a buffer containing 50 mM NaP pH 7.5, 150 mM NaCl. The run was performed at a flow rate of 1 ml/min. An activity test was performed by incubating 5 µl of every other fraction with 2 µg scBoNTA for 1 h at 37° C. and subsequent analysis on SDS-PAGE (FIG. 1). Fractions 6-24 were combined and its volume concentrated to 3.5 ml by using ultrafiltration (Amicon-Ultra MWCO 10,000).

(5) Size exclusion chromatography (SEC, HiLoad 16/60 Superdex 200): Subsequently, the concentrated protein solution of (4) was loaded on a HiLoad 16/60 Superdex 200 column, equilibrated with 50 mM NaP pH 7, 5, 150 mM NaCl. Separation was performed at a flow rate of 1 ml/min. Fractions with a retention volume between 80 ml and 100 ml were analysed using the activity test (1) and the appropriate fractions containing the enzymatic activity (nBH) were combined (~10 ml) and concentrated to 3 ml by ultrafiltration. Subsequently, ammonium sulphate was added to a final concentration of 12.5%=500 mM (+0.2 g).

(6) Hydrophobic interaction chromatography (HIC, HiTrap Phenyl Sepharose): nBH was bound to the Phenyl Sepharose in buffer A (50 mM NaP pH 7.5, 500 mM ammonium sulphate). Bound nBH was eluted by reducing the amount of ammonium sulphate due to a linear increasing gradient with buffer B (50 mM NaP pH 7.5) at a flow rate of 1 ml/min. All protein containing fractions were analysed using the activity test (1) and the appropriate fractions were combined and concentrated by ultrafiltration to 3.5 ml. The buffer of the solution was adjusted to 50 mM NaP pH 7.5; 150 mM NaCl.

Figure 2:
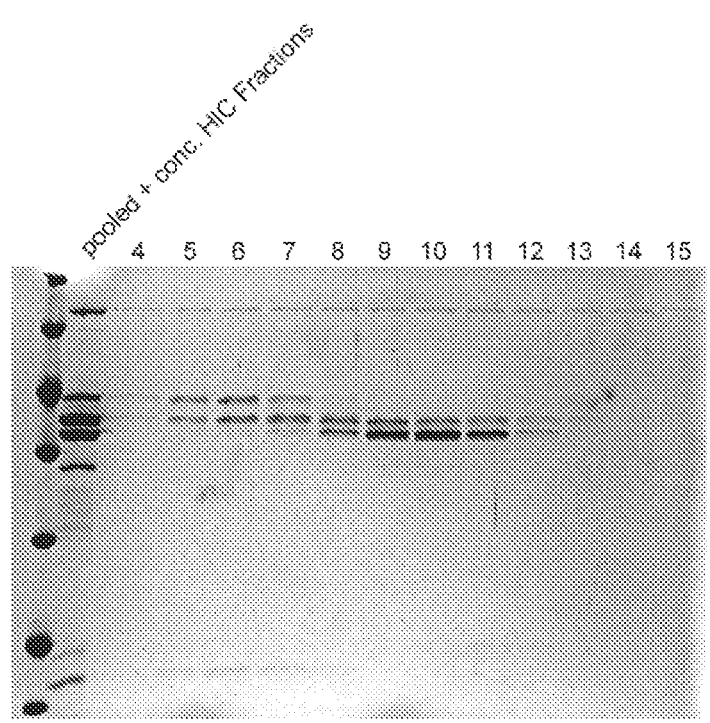
FIG. 2 depicts a 12.5% SDS-PAGE gel analysis of enzymatic activity in nBH-containing fractions collected following purification by size exclusion chromatography (SEC), followed by hydrophobic interaction chromatography (HIC) and further SEC, as described in Example 1. Collected fractions were incubated with single-chain BoNT/A and then loaded onto the gel (lane marked as "4" contains the fourth fraction collected, lane marked as "5" contains the fifth fraction collected, etc.). The left-most lane of the gel contains low molecular weight marker (LMW): 116 kDa, 66 kDa, 45 kDa, 35 kDa, 25 kDa, 18.4 kDa, and 14.4 kDa. The second-to-the-left lane contains single chain BoNT/A. The third-to-the-left lane contains proteins purified from lysed C. botulinum. The lanes containing the eighth to $12^{th}$ fractions show that single-chain BoNT/A had been converted into separate heavy (~100 kDa) and light (~50 kDa) chains.

(7) SEC (HiLoad 16/60 Superdex 75): Finally, the nBH was purified by SEC using the HiLoad 16/60 Superdex 75 column at 50 mM NaP pH 7.5, 150 mM NaCl and a flow rate of 1 ml/min. Fractions with a retention volume between 70 ml and 80 ml were analysed by 12.5% SDS-PAGE (FIG. 2) and the fractions 8-12 containing the nBH which migrates at 37.3 kDa were combined (~10 ml) and concentrated to 1 ml by ultrafiltration.

(8) The prominent protein migrating at approximately 37.3 kDa (nBH) was analysed by N-terminal peptide sequencing according to Edman degradation protocol. The sequence of the identified peptide is V Q G Q S V K G V G and corresponds to the first ten residues of SEQ ID NO: 1.

Figure 3:
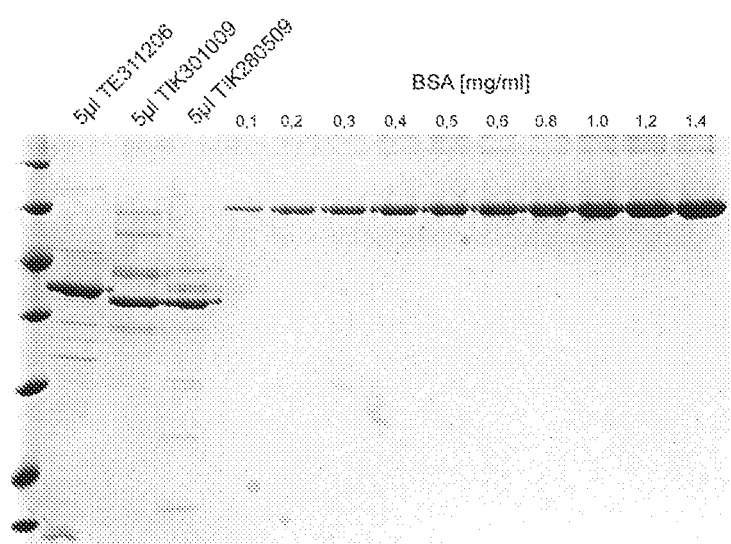
FIG. 3 depicts a SDS-PAGE analysis of three batches of nBH, purified as described in Example 1. The left-most lane contains low molecular weight marker (LMW): 116 kDa, 66 kDa, 45 kDa, 35 kDa, 25 kDa, 18.4 kDa, 14.4 kDa. The second-to-the-left lane contains purified nBH protein of Lot TE311206. The third-to-the-left lane contains purified nBH protein of Lot TIK301009 (130 ng/µl maturated NT02CB1447/CBO1445, SEQ ID NO: 1, amino acids 249-581 Genbank acc. CAL82988.1., MW: 37.3 kDa). The fourth-to-the-left lane contains purified protein of nBH lot TIK280509 (114 ng/µl maturated NT02CB1447/CBO1445, SEQ In NO: 1, amino acids 249-581 of Genbank acc. CAL82988.1, MW: 37.3 kDa). The remaining lanes contain increasing amounts of bovine serum albumin (BSA) to indicate the staining density produced by known amounts of a standard protein.

(9) Two lots of nBH (NT02CB1447, 37.3 kDa, FIG. 3, lane 3: TIK301009, lane 4: TIK280509) were reproducibly isolated according to the procedure as described above. Following modifications of the isolation procedure yields the nBH isoform NT02CB1446 (38.6 kDa, FIG. 3, lane 2, lot TE311206): (i) growth of *C. botulinum* culture: 18 h instead of 48 to 72 h; (ii) variation of chromatographic steps: IEC→SEC Superdex 75→HIC Phenyl Sepharose instead of IEC→SEC Superdex 200→HIC Phenyl Sepharose→SEC Superdex 75.

Example 2

Sequence Identification of nBH from *C. botulinum* by Mass Spectrometry (MS)

(1) Tryptic digestion: The protein bands migrating at approximately 38 kDa (nBH) in SDS-PAGE were excised for tryptic digestion and destained by gently shaking in 50 mM $NH_4HCO_3$, 50% acetonitrile for 30 min at 37° C. Destaining was repeated until gel spots were clear. Acetonitrile (100%) was added and removed after 3 min. Subsequently, spots were dried in a speed vac system (Eppendorf, Germany). Trypsin (10 ng/μl) in 50 mM $NH_4HCO_3$ was added and incubated on ice for 1 h. Then, the remaining trypsin solution was removed, a small volume 50 mM $NH_4HCO_3$ was added and digestion was carried out at 37° C. over night. The supernatant was collected and gel pieces were extracted using 5% TFA, 10% acetonitrile for two times. All fluids were combined, dried in a speed vac and extracted peptides were stored at 4° C.

(2) Matrix assisted laser desorption ionisation time of flight (MALDI-TOF/TOF) MS: Samples were analyzed in an MALDI-TOF/TOF mass spectrometer (Ultraflex1 Bruker Daltonik GmbH) in linear mode with an acceleration voltage of 25 kV. Masses were detected from 700 m/z to 4,500 m/z. Samples (2 μl) were cocrystallised with 2 μl of sinnapinic acid solution containing 50% acetonitril and 0.2% trifluoric acetic acid (TFA) directly on a stainless steel MALDI target plate. 500 laser shots were collected for each sample.

(3) Peptide separation by reversed phase chromatography: Peptide separation was done by reversed phase chromatography using a nano-HPLC system (Agilent Technologies, Waldbronn, Germany) that consist of an autosampler and a gradient pump. The sample was dissolved in buffer A (5% acetonitril, 0.1% formic acid) and an aliquot of up to 10 μl was injected onto a C18 column (Zorbax SB-C18, 5 μm, 300 A, 0.5 mm inner diameter, length 15 cm) at a flow rate of 5 μl/min. After loading, the column was washed for 15 min with buffer A and the peptides were eluted using a gradient of eluent A and eluent B (70% (v/v) acetonitrile in 0.1% (v/v) formic acid) from 0% to 100% eluent B in 75 min.

(4) Electrospray ionisation (ESI)-interface and ion trap mass spectrometry: The HPLC outlet was directly connected to the nanoESI source of an ion trap mass spectrometer and the Agilent coaxial sheath-liquid sprayer was used (Agilent Technologies). The outlet capillary was hold by a surrounding steel needle and looked 0.1 to 0.2 mm out of it. The spray was stabilized by $N_2$ as nebulizer gas (5 l/min). Ionization voltage was set to 4,500 V and dry gas was applied at 5 psi and 250° C. Spectra were collected with an Esquire3000+ ion trap mass spectrometer (Bruker Daltonik) at a scan speed of 13,000 m/z per second. Using ESI in positive mode, mass spectra were acquired from 50 to 1600 m/z in scanning mode and data dependent switching between MS and MS/MS analysis. To increase the quality of MS/MS spectra only two precursor ions from one spectrum were selected for MS/MS analysis and active exclusion was set to 2 min to exclude precursor ions that had already been measured.

(4) Data processing: Data processing was performed with the Data Analysis (version 3.0) and BioTools (version 3.0) software packages (Bruker Daltonik). Protein identification was done using MASCOT software (version 2.1) and MSDB data base (Matrix Science, London, UK).

(5) Results:

TABLE 2 nBH identified by MS

| lane | Lot nBH | Protein concentr. | Name of ORF | Genbank acc. | aa of ORF | MW [kDa] | Mascot score |
|---|---|---|---|---|---|---|---|
| 2 | TE311206 | 192 ng/μl | NT02CB1446 CBO1444 | CAL82987.1 | 254-594 | 38.6 | 725 |
| 3 | TIK301009 | 130 ng/μl | NT02CB1447 CBO1445 | CAL82988.1 | 249-581 | 37.3 | 555 |
| 4 | TIK280509 | 114 ng/μl | NT02CB1447 CBO1445 | CAL82988.1 | 249-581 | 37.3 | 609 |

The 38.6 kDa protein band of lane 2 (nBH lot TE311206) was identified as NT02CB1446/CB01444 with a Mascot score of 725 and a peptide MS/MS sequence coverage of 29.6% over the entire open reading frame (ORF). No peptide was identified derived from the N-terminal 253 amino acids (FIG. 4). The MS/MS analysis of lot TE311206 displayed a sequence coverage of 52% according to the C-terminal amino acids 254-594 forming the nBH.

The 37.3 kDa protein bands of lane 3 (nBH lot TIK301009) and lane 4 (nBH lot TIK280509) were identified as NT02CB1447/CB01445 with a Mascot score of 555 and 609, respectively. Except one all peptides identified derive from the C-terminal 333 amino acids (FIG. 5). The MS/MS analysis of lot TIK301009 displayed a sequence coverage of 49.5% according to the C-terminal amino acids 249-581 forming the nBH.

Example 3

Figure 6A:
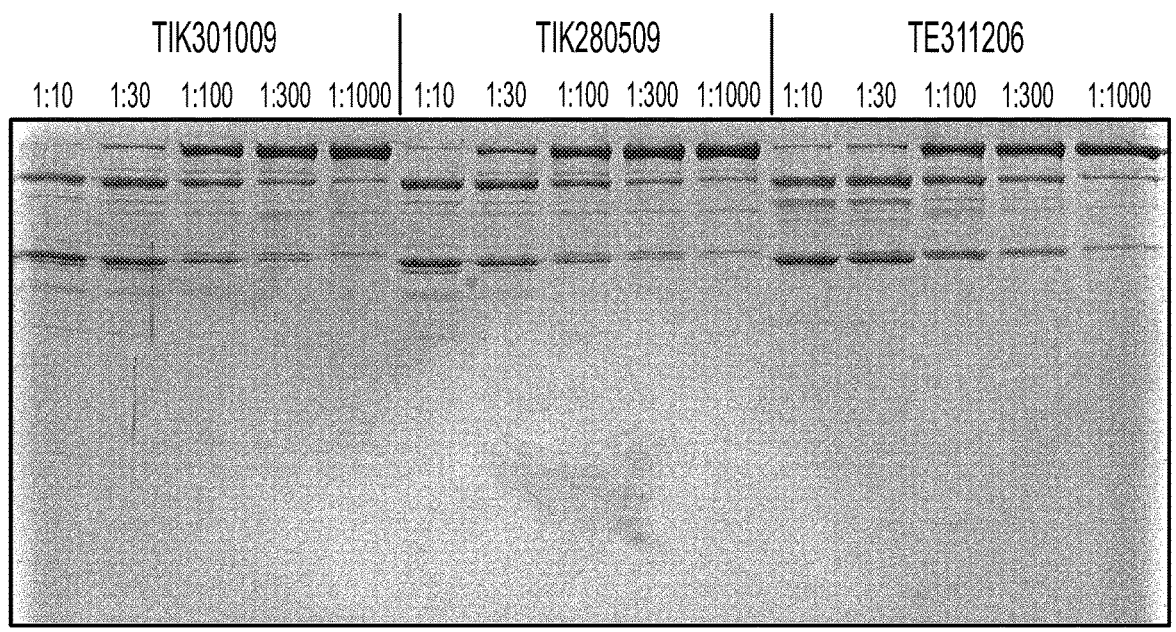
FIG. 6A depicts a SDS-PAGE gel analysis of the proteolytic activity of nBH derived from the TIK301009, TIK280509, and TE311206 lots. Purified nBH was incubated with single-chain BoNT/A at the following nBH to single-chain BoNT/A ratios: 1:10, 1:30, 1:100, 1:300, and 1:1000. Increasing concentrations of nBH led to increasing conversion of single-chain BoNT/A into heavy (~100 kDa) and light (~50 kDa) chain species.
Figure 6B:
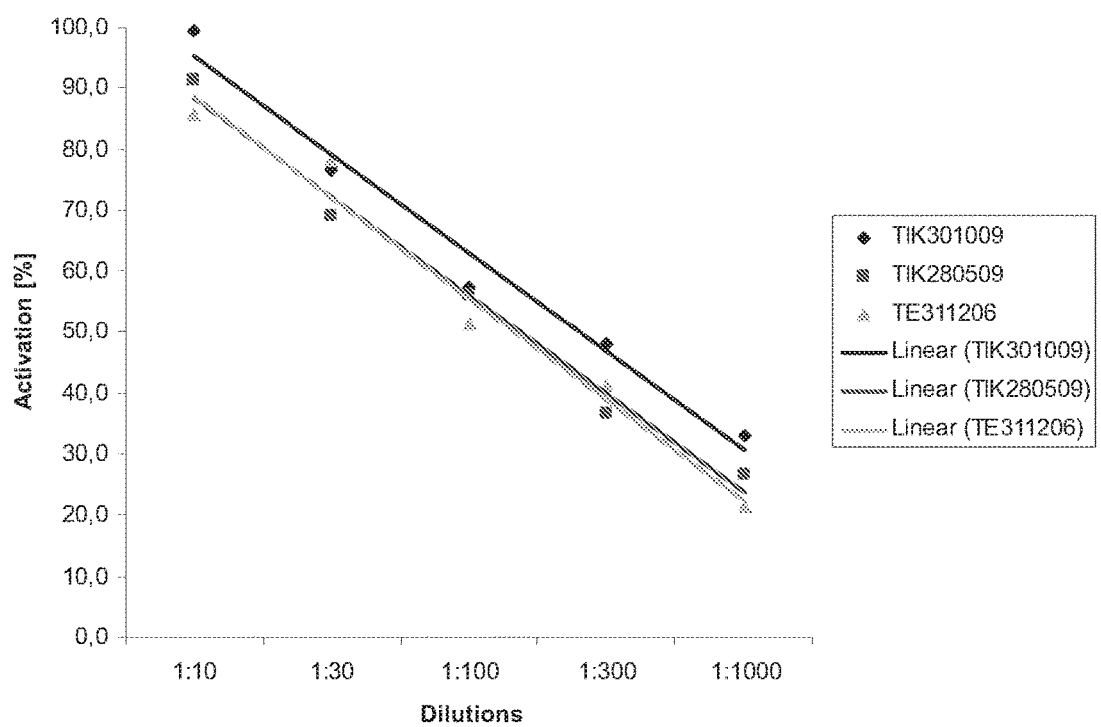
FIG. 6B depicts the % of active BoNT/A (as measured by the sum of the optical density of the bands representing BoNT/A heavy and light chains divided by sum of the optical density of the bands representing BoNT/A heavy and light chains and single-chain BoNT/A) plotted against the ratio of purified nBH to single-chain BoNT/A in the reaction mixture. The specific proteolytic activity of the three different batches is nearly identical.

Characterisation of Enzymatic Specificity of nBH (1) The concentration dependent proteolytic activity of nBH derived from three purification batches was compared (FIGS. 6A and B). An activity test analysing nBH derived from the batches TIK301009, TIK280509 and TE311206 using various dilutions of nBH demonstrates that higher dilutions decrease the cleavage rate. The assay was performed by incubating 1 μg scBoNT/A and 2 μl $dH_2O$ and 1 μl of correspondingly diluted nBH for 60 mm at 37° C. For SUS-PAGE analysis, 3 μl of a reducing 4×SDS Laemmli buffer was added to a final volume of 10 μl. 150 kDa scBoNT/A was cleaved into 100 kDa heavy chain and 50 kDa light chain. The proteolytic activity of the three different batches is nearly identical indicating that the maturated isoform NT02CB1446 (TE311206) displays a similar specific activity as the maturated NT02CB1447 (SEQ ID NO: 1).

(2) The time-dependent cleavage of scBoNT/A wild-type and mutants by nBH was analysed employing the activity test (FIGS. 7 A, B, and C). scBoNTAS wild-type is activated by nBH in a time dependent manner into light chain and heavy chain within 120 min by more than 95%. The loop sequence was modified to characterise the cleavage site. In scBoNTAS Throm all lysine residues are removed and the thrombin recognition sequence LVPRGS is inserted which prolonged the cleavage rate. In scBoNT Res the loop lacks any basic amino acids which drastically delays the complete hydrolysis indicating a strong recognition preference of nBH for basic residues like lysine and arginine at the cleavage site. Furthermore, accessibility of nBH to the loop by is impaired by shortening the loop to eight small residues or five amino acids with bulky side chains (scBoNTAS (GGSG)$_2$ and scBoNTAS FQWYI).

Figure 8A:
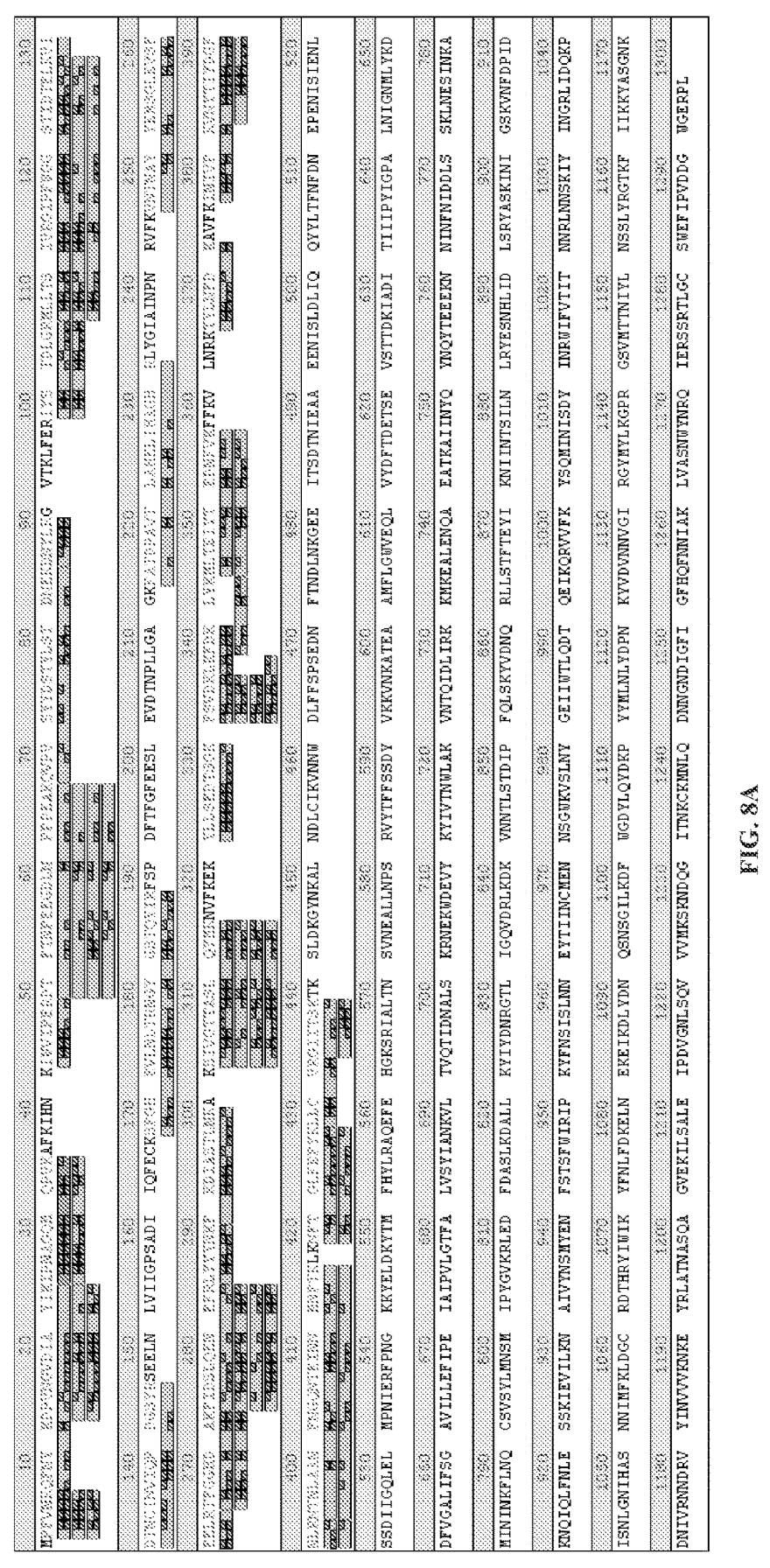
Figure 8B:
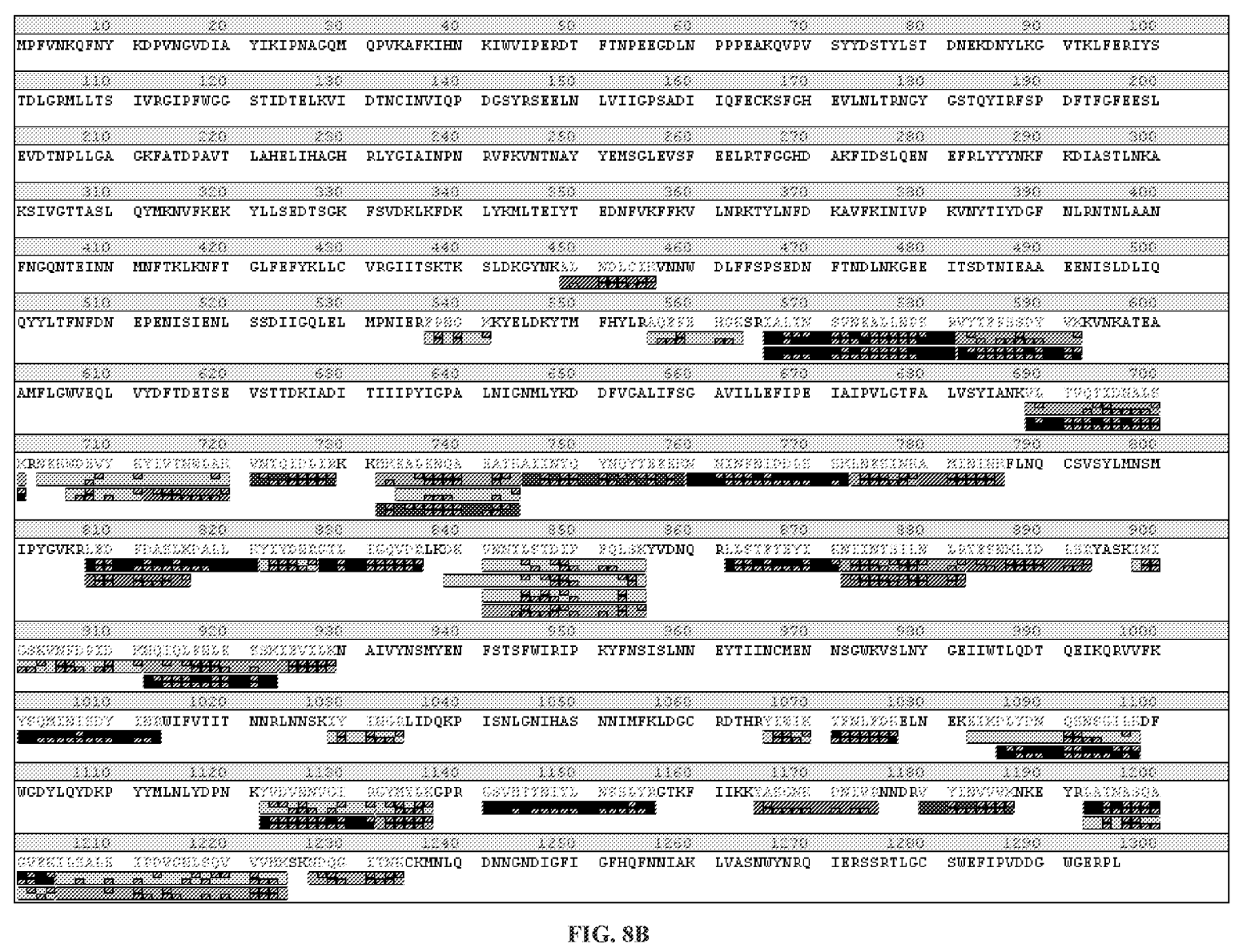

(3) The MS/MS analysis of the 50 kDa cleavage product upon digestion of scBoNT/A with nBH exhibited that the most C-terminal ascribed peptide covers amino acids G433 to K438 which corresponds to the physiologically observed C-terminus of BoNT/A LC (FIG. 8A). Analysis of the 100 kDa cleavage product which was identified as heavy chain of BoNT/A demonstrated that the most N-terminal ascribed peptide covers amino acids A449 to K456 which corresponds to the physiologically observed N-terminus of BoNT/A HC (FIG. 8B). Thus, the isolated nBH yields physiologically processed BoNT/A and preferentially hydrolyses peptide bonds C-terminal to lysine and arginine residues.

Example 4

Evolutionary Conservation of BoNTHydrolase and its Isoforms

Protein sequence analysis of SEQ ID NO: 2 (Genbank acc. CAL82988.1/YP_001253958.1) revealed three conserved domains. Residues 18-573 correspond to a Zinc metalloprotease (elastase) or LasB involved in amino acid transport and metabolism with a Blast score of 738. Residues 148-212 correspond to a peptidase propeptide and YPEB domain or PepSY (Blast score 97. Residues 336-573 are part of the peptidase M4 family including thermolysin, proteailysin, aureolysin and neutral proteases (Blast score 803).

The genome sequencing of C. botulinum ATCC 3502 has revealed the existence of six ORFs encoding iBH isoforms (Sebaihia et al., 2007, Genome Res. 17(7):1082-1092). Further genome data is available for 10 group I C. botulinum strains as well as the non-BoNT secreting C. sprogenes which all contain between five to seven ORFs encoding iBH. The nBH (SEQ ID NO: 1) shares minimum 64% amino acid sequence identity with the other 63 isoforms.

Example 5

Figure 9A:
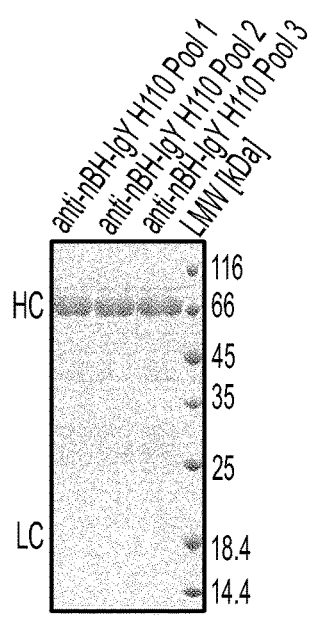
FIG. 9A is a SDS-PAGE analysis of proteins from samples (Pools 1-3) collected from the eggs of chicken immunized with nBH as described in Example 5.

Generation of Antibodies Specific for the BoNTHydrolase (1) Generation of IgY: Sixteen-week-old chickens [ISA Brown and Lohmann Selected Leghorn (LSL), Spreenhagener Vermehrungsbetrieb fur Legehennen GmbH, Bestensee, Germany] were kept in individual cages, exclusively constructed for the maintenance of chickens (Ebeco, Castrop-Rauxel, Germany). Food (ssniff Legehühner-Zucht 1 and 2; ssniff Spezialitaten GmbH, Soest, Germany) and water were available ad libitum, and the chickens started laying eggs between 23 and 25 weeks of age. Eggs were collected daily, labelled, and stored at 4° C. until they were further processed. All animal maintenance and experiments were performed in accordance with the guidelines of local authorities, Berlin (No. H0069/03). Chickens were immunized and boosted via the i.m. route (pectoralis muscle, left and right side) a total of 10 times over a 1-year period, with intervals between 4 and 8 weeks. The interval used was based on previous work that showed no demonstrable memory cells until at least 3 weeks postimmunisation (Pei and Collisson, 2005). The antigen concentration used was approximately 20 µg per injection (nBH). No more than 500 µl of antigen solution was injected per immunization. Freund's complete adjuvant was used for the first immunisation, and FIA was used for the subsequent booster injections. The method for IgY purification was adapted from Polson et al. (1980). Briefly, the egg yolk was diluted 1:2 with sterile PBS (pH 7.4, Roche, Mannheim, Germany). For elimination of lipids and lipoprotein, 3.5% (w/v) polyethylene glycol (PEG) 6000 (Roth, Karlsruhe, Germany) was added. After gentle shaking followed by centrifugation (10,000×g for 20 min at 4° C.), the supernatant was decanted and solid PEG 6000 was added to a final concentration of 12% (w/v). This mixture was then centrifuged as above. The precipitate was dissolved in 10 ml of PBS, PEG was added to 12% (wt/vol), and the solution was centrifuged. Finally, the precipitate was dissolved in 1.2 ml of PBS, transferred into a microdialysis device (QuixSep, Roth, Germany) and dialysed against PBS at 4° C. The protein content (mg/ml) was analysed by 12.5% SDS-PAGE (FIG. 9A) and measured photometrically at 280 nm and was calculated according to the Lambert-Beer law with an extinction coefficient of 1.33 for IgY.

Figure 9B:
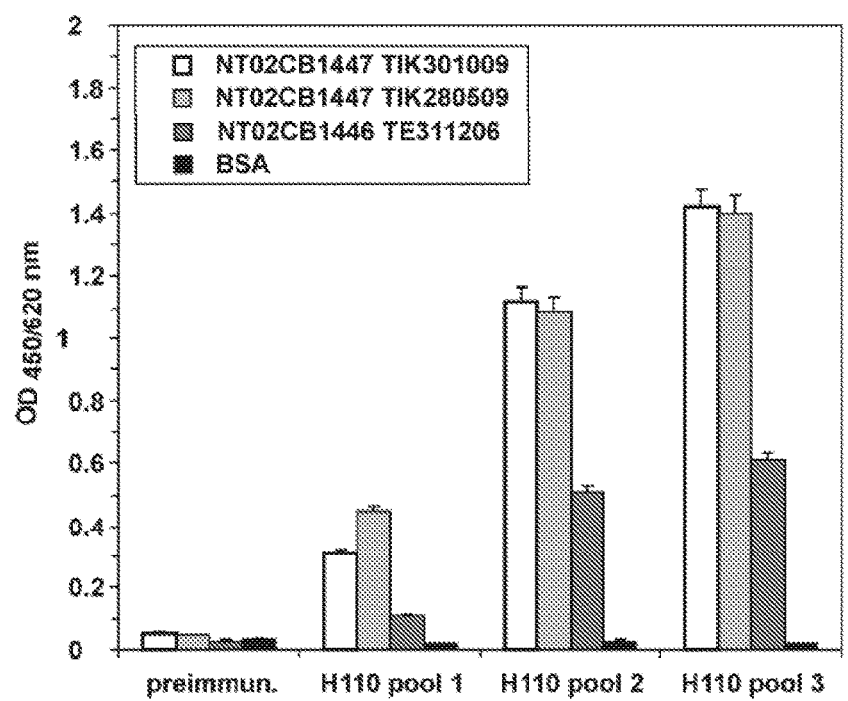
FIG. 9B depicts the results of an ELISA of the binding of antibodies from Pools 1-3 to nBH derived from the TIK301009, TIK280509, and TE311206 lots (NT02CB1447, NT02CB1447, and NT02CB1446, respectively). The low "preimmun." bars show that there are no other molecules in chicken eggs that bind appreciably to nBH (i.e., similar to BSA). Pool 1 binds the least nBH whereas pool 3 binds the most nBH.

(2) ELISA: Nunc Maxisorp F96 microtiter plates (VWR International GmbH, Darmstadt, Germany) were coated with nBH of various lots (500 ng/mL) in PBS overnight at 4° C. and then blocked for 1 h with blocking buffer of PBS containing 0.1% Tween-20 and 2% nonfat skimmed milk (Merck, Darmstadt, Germany). After washing, a IgY dilution (10 µg/ml in blocking buffer) was added for 1 h and detected using biotin-labeled donkey antichicken IgY, streptavidin-horseradish peroxidase (both Dianova, Hamburg, Germany) and 3,3',5,5'-tetramethylbenzidine (Sigma). Detected nBH is illustrated in FIG. 9B.

(3) Western blot: nBH was separated per 12.5% SDS-PAGE, and were transferred onto a polyvinylidene fluoride membrane (Invitrogen GmbH, Karlsruhe, Germany) using standard immunoblotting techniques. The membrane was blocked overnight at 4° C., and incubated with IgY (1:5,000 in blocking buffer) for 1 h. After washing, the membrane was probed with biotin-labelled donkey antichicken IgY for 30 min and was developed using alkaline phosphatase and CDP-Star (Perkin Elmer, Waltham, Mass.).

Example 6

Recombinant Expression of BoNTHydrolase (1) Plasmid constructions: The gene portions encoding native BH (SEQ ID NO: 1) and its propeptide (SEQ ID NO: 2) were amplified by PCR using suitable oligonucleotides and genomic DNA of C. botulinum ATCC 3502, fused to an oligonucleotide coding for the His6Tag and inserted into pQE3 (Qiagen) yielding the expression plasmid pQ-BH1445H6-249-581 and pQ-BH1445H6-1-581, respectively. Nucleotide sequences were verified by DNA sequencing.

Figures 10A, 10B:
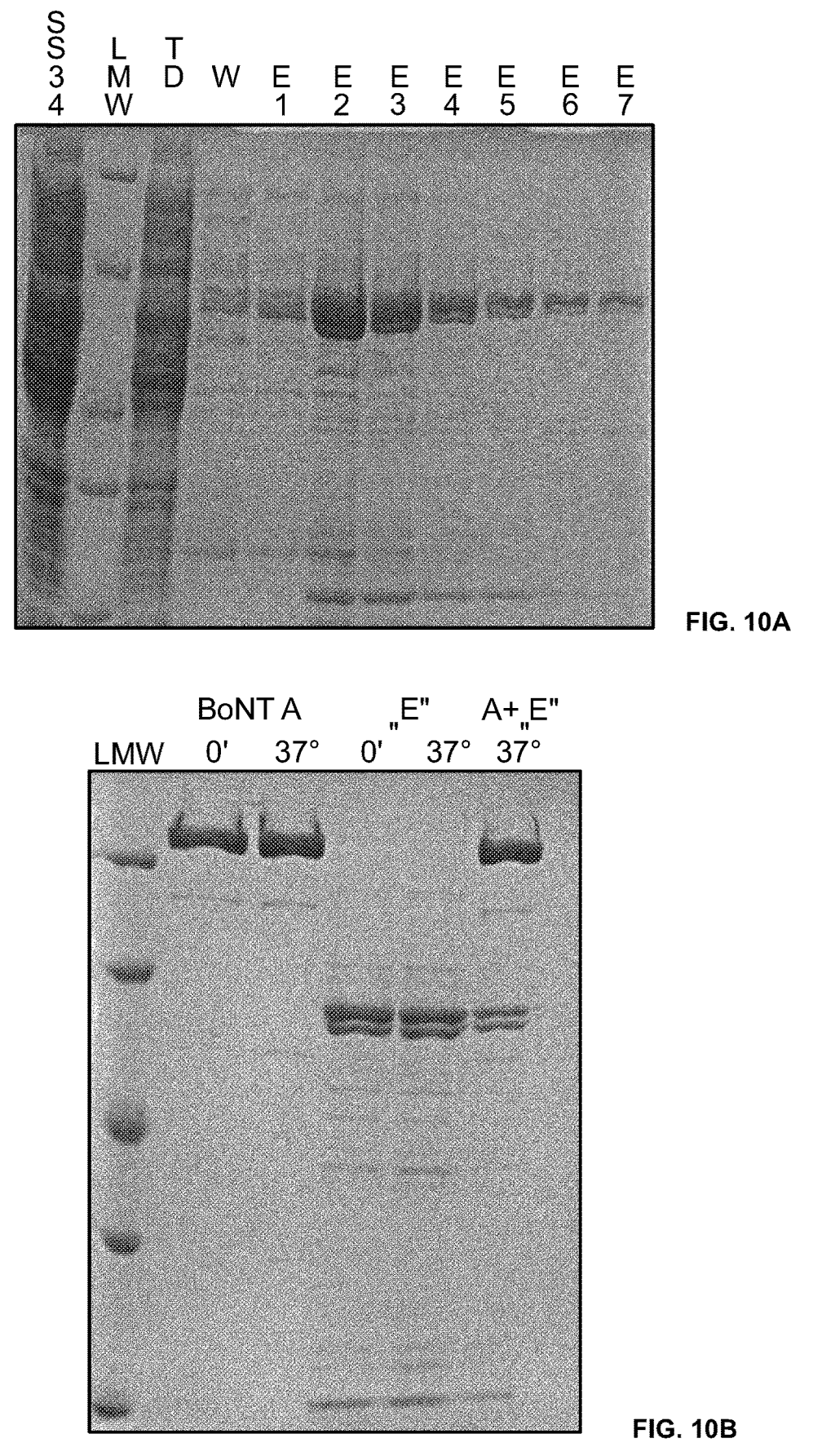

(2) Purification of recombinant proteins: nBH and iBH, fused to a carboxyl-terminal His6Tag, were produced utilizing the *E. coli* strain M15pREP4 (Qiagen) during ten hours of incubation at room temperature, and were purified on Talon-sepharose beads (Clontech Inc.) following to the manufacturer's instructions. Fractions containing the desired proteins were pooled, frozen in liquid nitrogen, and kept at −70° C. iBH was isolated as recombinant protein with a MW of 63 kDa (FIG. 10A). The inactivity of iBH was demonstrated using the activity test: after 1 h at 37° C. no scBoNT/A wt was hydrolysed in LC and HC (FIG. 10B).

Example 7

Inhibition of BoNTHydrolase (1) Screening for peptide inhibitors of BH: Peptides based on SEQ ID NOs: 4 to 25 will be synthesised lacking one or more basic residues. Each peptide will be added to the mixture according to the activity test. A peptide being able to decrease the amount of processed scBoNT/A, prolong the duration required for fully processing scBoNT/A or block processing scBoNT/A is considered to be an inhibitor of nBH.

(2) Screening for antibody-based inhibitors: Antibodies generated against epitopes derived from nBH like IgY of Example 5 are incubated with nBH and subsequently subjected to the activity test. An antibody being able to decrease the amount of processed scBoNT/A, prolong the duration required for fully processing scBoNT/A or block processing scBoNT/A is considered to be an inhibitor of nBH.

Example 8

Figure 11A:
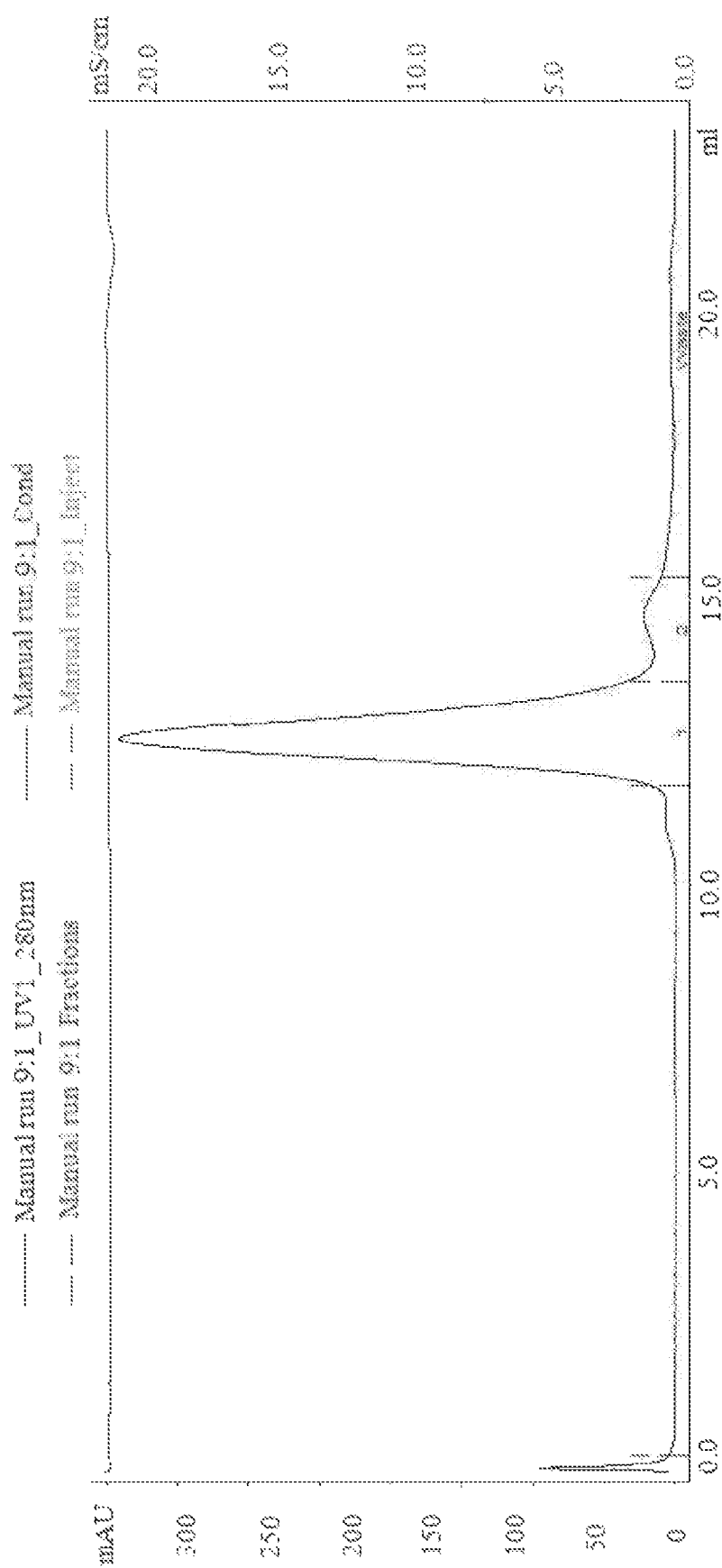
FIG. 11A is a chromatogram of size exclusion chromatography conducted following incubation of single-chain BoNT/A with recombinant BH for 12 minutes at 37° C. The y-axis indicates the absorption of light at 280 nm, indicating the presence of protein, and the x-axis indicates the volume of buffer that has passed through the column.
Figure 11B:
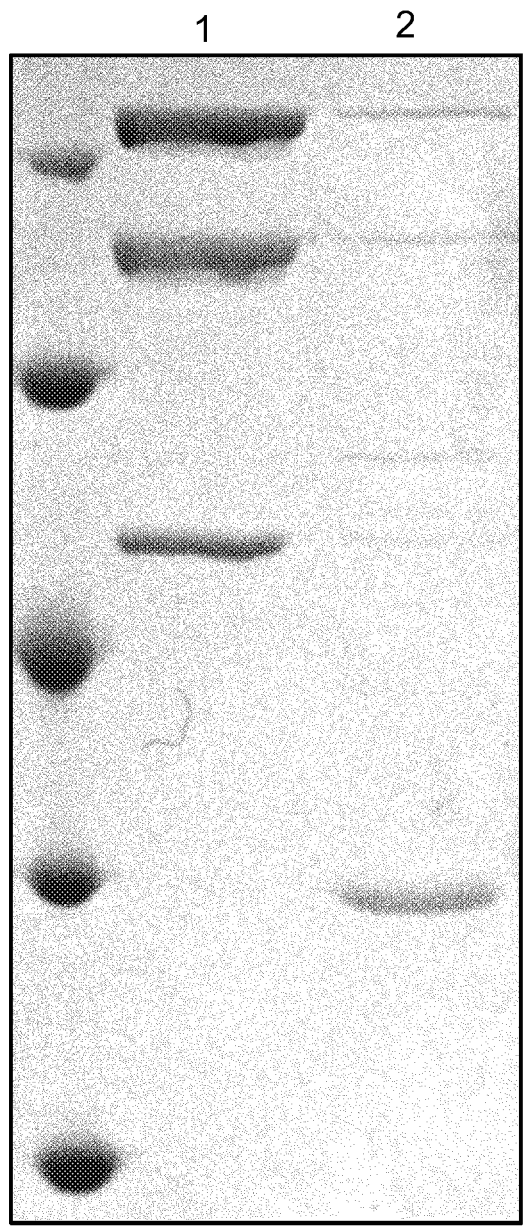
FIG. 11B is an SDS-PAGE analysis conducted on two fractions collected that correspond to the peaks shown in the chromatogram of FIG. 11A. The gel shows that fraction 1 contains single-chain BoNT/A and some di-chain BoNT/A (~40% activation) and fraction 2 contains BH at <40 kDa. The left-most lane contains the molecular weight ladder.
Figure 11C:
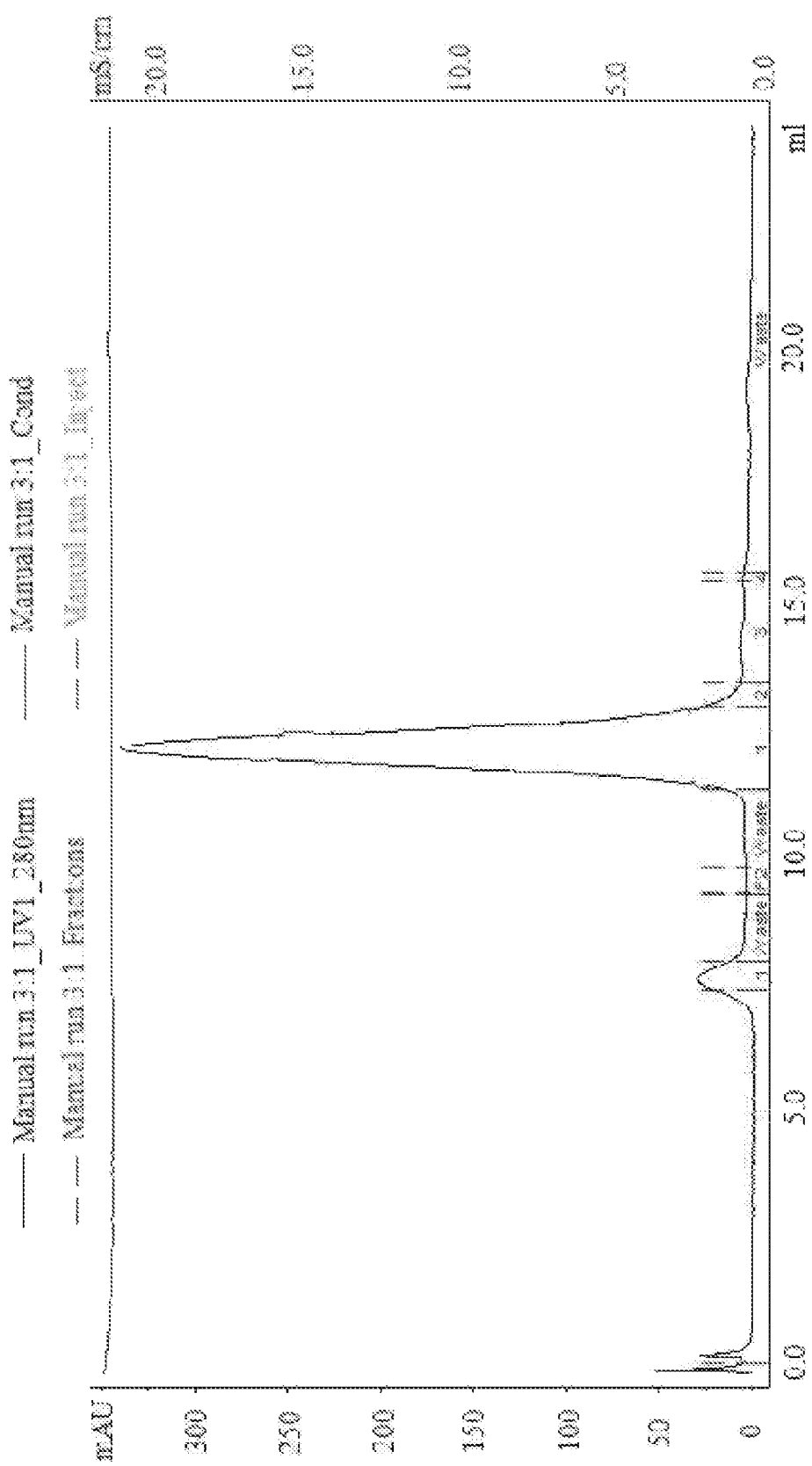
FIG. 11C is a chromatogram of size exclusion chromatography conducted following incubation of the 40% activated BoNT/A, collected from the fraction corresponding to Peak 1 of FIG. 11A, with recombinant BH for 15 minutes at 37° C. The y-axis indicates the absorption of light at 280 nm, indicating the presence of protein, and the x-axis indicates the volume of buffer that has passed through the column.

Use of Purified Active Bonthydrolase (nBH) for Obtaining Proteolytically Processed Polypeptide (1) 200 µg of recombinant purified scBoNT/A is incubated with 350 ng purified active BoNTHydrolase for 12 min at 37° C. To stop the reaction nBH is removed by SEC (column Superdex 200 10/300 GL, buffer: 50 mM NaP pH 7.5, 150 mM NaCl, sample volume=0.3 ml, flow rate=0.25 ml/min) and the amount of cleavage is analysed by 10% SDS-PAGE (FIG. 11B).

Figure 11D:
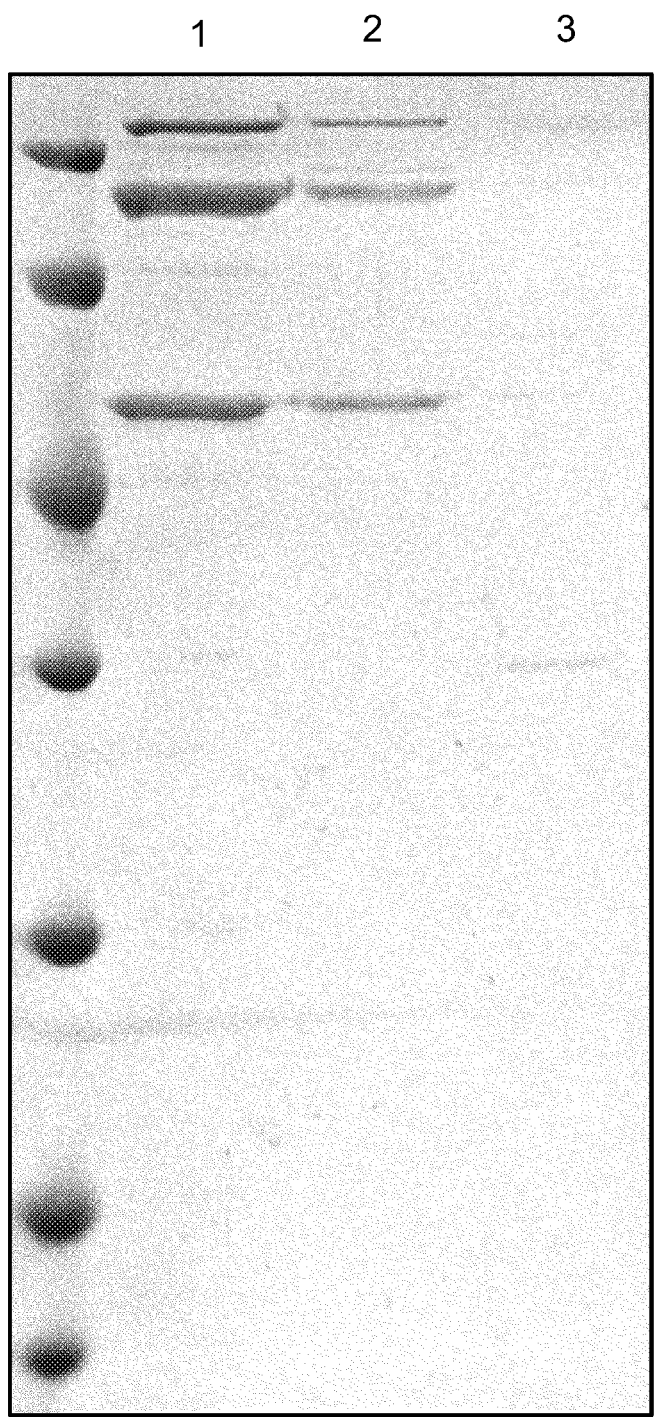
FIG. 11D is an SDS-PAGE analysis conducted on three fractions collected during the chromatography. The fractions that correspond to the main peak (fractions 1 and 2) indicate that about 80% of the BoNT/A is in di-chain form (~80% activation).
Figure 11E:
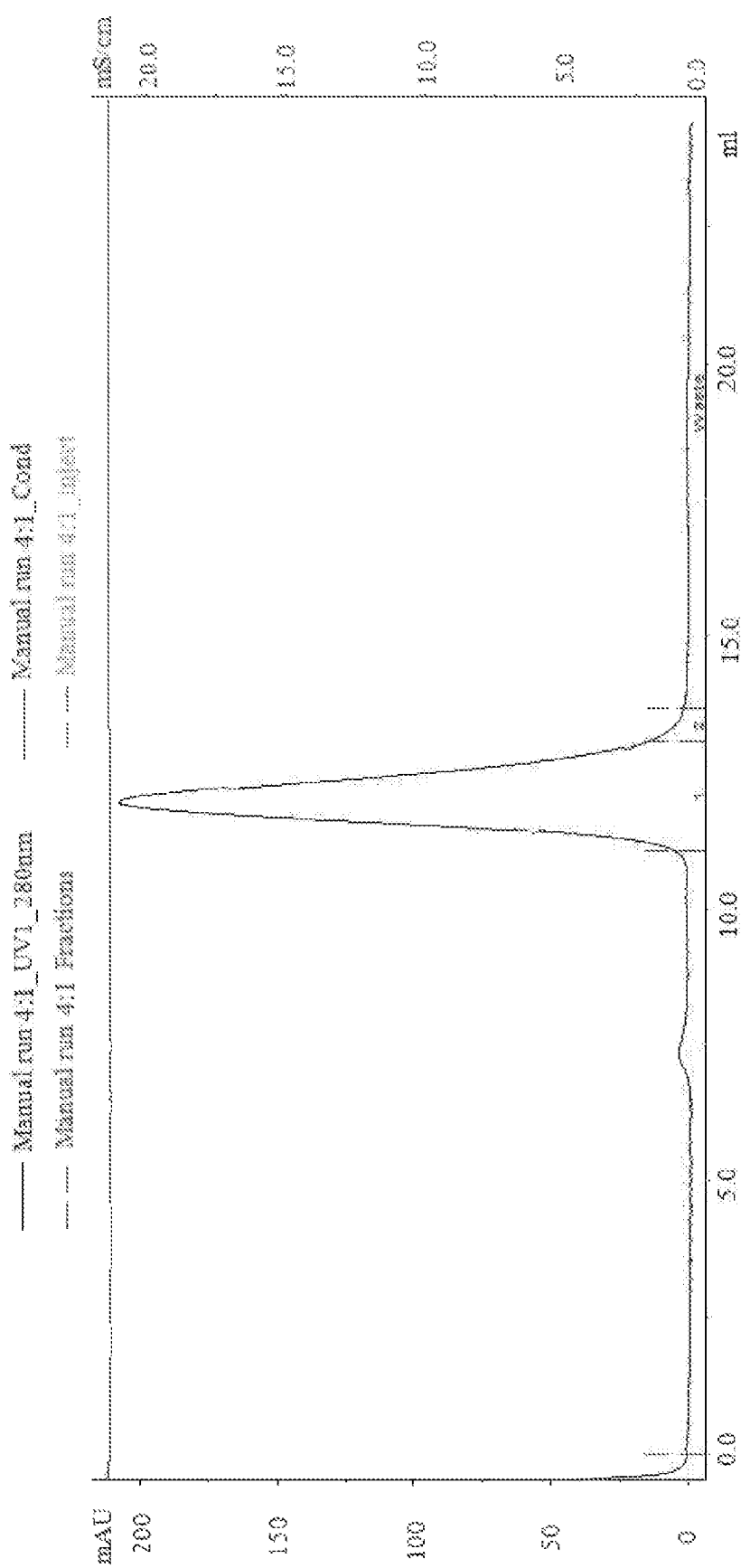
FIG. 11E is a chromatogram of size exclusion chromatography conducted following incubation of the ~80% activated BoNT/A, collected from the fractions corresponding to the main peak of FIG. 11C (fractions 1 and 2 described in FIG. 11D), with recombinant BH for 25 minutes at 37° C. The y-axis indicates the absorption of light at 280 nm, indicating the presence of protein, and the x-axis indicates the volume of buffer that has passed through the column.

(2) Fraction 1 (1800 µl) containing 40% processed BoNT/A is incubated with 350 ng purified active BoNTHydrolase for 15 min at 37° C. and concentrated to 300 µl by ultrafiltration. To finally stop the reaction nBH is removed by SEC (column Superdex 200 10/300 GL, buffer: 50 mM NaP pH 7.5, 150 mM NaCl, sample volume=0.3 ml, flow rate=0.25 ml/min) and the amount of cleavage is analysed by 10% SDS-PAGE (FIG. 11D).

Figure 11F:
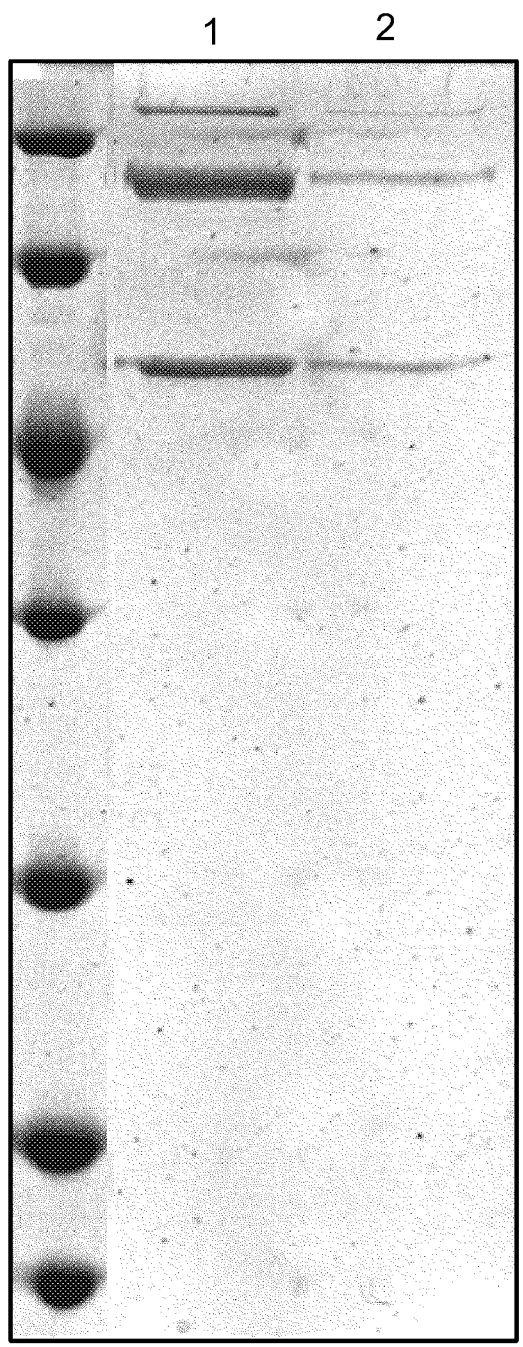
FIG. 11F is an SDS-PAGE analysis conducted on the two fractions collected during the chromatography that correspond to the main peak in FIG. 11E. The gel indicates that about 95% of the BoNT/A is in di-chain form (~95% activation).

(2) Fractions 1 and 2 (1800 µl) containing 80% processed BoNT/A are combined and incubated with 120 ng purified active BoNTHydrolase for 25 min at 37° C. and concentrated to 300 µl by ultrafiltration. To finally stop the reaction nBH is removed by SEC (column Superdex 200 10/300 GL, buffer: 50 mM NaP pH 7.5, 150 mM NaCl, sample volume=0.3 ml, flow rate=0.25 ml/min) and the amount of cleavage is analysed by 10% SDS-PAGE (FIG. 11F). A >95% processed BoNT/A (Seq ID NO. 3) is obtained. The identical fully processed second polypeptide (>95% processed BoNT/A) is obtained if the second polypeptide is processed in one step for 50 min at 37° C. (200 µg scBoNT/A incubated with 350 ng nBH). After an incubation time of 1 h at 37° C., more than 97% of BoNT/A is processed.

The invention claimed is:

1. A method for producing a proteolytically processed polypeptide, the method comprising contacting a first polypeptide having at least 50% sequence identity with SEQ ID NO: 1 with a second polypeptide that is susceptible to proteolysis by the first polypeptide, resulting in the proteolytic processing of the second polypeptide into at least two cleavage products; wherein: the method occurs in vitro; and/or at least one of the first or second polypeptide is recombinant or purified.

2. The method of claim 1, wherein the second polypeptide comprises an amino acid sequence having at least 50% sequence identity swill any one of SEQ ID NOs: 3 to 25.

3. The method of claim 1, wherein the second polypeptide is a clostridial neurotoxin.

4. The method of claim 1, wherein the second polypeptide is selected from: a clostridial neurotoxin polypeptide that lacks a functional binding domain ($H_{cc}$), a clostridial neurotoxin polypeptide that has a modified clostridial neurotoxin binding domain ($H_{cc}$) that binds to a native clostridial neurotoxin receptor; or a clostridial neurotoxin polypeptide having a non-clostridial binding domain that binds to a non-native clostridial neurotoxin receptor.

5. The method of claim 4, wherein the clostridial neurotoxin comprises a light chain from a first clostridial neurotoxin serotype and/or sub-type and a heavy chain from a second and different clostridial neurotoxin serotype and/or subtype.

6. The method of claim 1, wherein the second polypeptide is a single-chain clostridial neurotoxin prepared by recombinant expression in *E. coli*.

7. The method of claim 1, wherein the first polypeptide is purified and has 100% sequence identity to SEQ ID NO: 1.

8. The method of claim 1, wherein the second polypeptide recombinant.

9. The method of claim 1, wherein die second polypeptide is recombinant BoNT/A.

10. A method for proteolytically processing a polypeptide in a subject wherein a first polypeptide having at least 50% sequence identity with SEQ NO: 1 and a second polypeptide that is susceptible to proteolysis by the first polypeptide are both administered to a subject and allowed to contact each other, resulting in the proteolytic processing of the second polypeptide into at least two cleavage products.

11. The method of claim 1, wherein the First and second polypeptides are incubated together for at least 30 minutes.

12. The method of claim 9, wherein the first polypeptide has at least 85% sequence identity with SEQ ID NO: 1.

13. The method of claim 1, wherein the first polypeptide has at least 90% sequence identity with SEQ ID NO: 1.

14. The method of claim 1, wherein the first polypeptide has at least 95% sequence identity with SEQ ID NO: 1.

15. The method of claim 1, wherein the first polypeptide comprises an amino acid sequence that differs from that of SEQ ID NO: 1 by up to 50 conservative amino acid exchanges.

16. The method of claim 1, wherein the first polypeptide comprises an amino acid sequence that differs from that of SEQ ID NO: 1 by up to 20 conservative amino acid exchanges.

17. The method of claim 1, wherein the first polypeptide comprises an amino acid sequence that differs from that of SEQ ID NO: 1 by up to 10 conservative amino acid exchanges.

18. The method of claim 10, wherein the first polypeptide has at least 95% sequence identity with SEQ ID NO: 1.

19. The method of claim 10, Wherein the first polypeptide comprises an amino acid sequence that differs from that of SEQ ID No: 1 by up to 20 conservative amino acid exchanges.

20. The method of claim 10, wherein the first polypeptide comprises an amino acid sequence that differs from that of SEQ ID NO: 1 by up to 10 conservative amino acid exchanges.

* * * * *

SEQUENCE LISTING

<160> NUMBER OF SEQ ID NOS: 27

<210> SEQ ID NO 1
<211> LENGTH: 333
<212> TYPE: PRT
<213> ORGANISM: Clostridium Botulinum

<400> SEQUENCE: 1

```
Val Gln Gly Gln Ser Val Lys Gly Val Gly Lys Thr Ser Leu Asp Gly
1               5                   10                  15

Leu Val Asn Ile Asp Val Thr Tyr Gly Asn Gly Lys Tyr Tyr Leu Lys
            20                  25                  30

Asp Ser Asn Lys Asn Ile Tyr Leu Tyr Asp Leu Lys Asn Gln Val Asp
        35                  40                  45

Glu Tyr Asp Leu Tyr Asn Tyr Leu Ser Arg Pro Asn Tyr Lys Gln Ile
    50                  55                  60

Leu Met Ser Lys Ser Glu Leu Ile Ser Asn Tyr Asn Asn Phe Ile
65                  70                  75                  80

Ala Asn Asn Gln Val Asn Ser Val Asp Ala Tyr Val Asn Thr Asn Lys
            85                  90                  95

Thr Tyr Asp Tyr Tyr Lys Asn Lys Leu Asn Arg Asn Ser Ile Asp Asn
            100                 105                 110

Lys Gly Met Asn Ile Asn Gly Phe Val His Val Gly Arg Asn Tyr Gly
            115                 120                 125
```

-continued

```
Asn Ala Phe Trp Tyr Gly Pro Tyr Asp Gly Met Phe Phe Gly Asp Gly
            130                 135                 140

Asp Gly Ile Tyr Phe Ser Ser Leu Ala Lys Ser Leu Asp Val Val Gly
145                 150                 155                 160

His Glu Leu Ser His Gly Val Thr Asn Lys Glu Ser Asn Leu Lys Tyr
                165                 170                 175

Glu Asn Glu Ser Gly Ala Leu Asn Glu Ser Phe Ser Asp Ile Met Gly
            180                 185                 190

Val Ala Val Glu Gly Lys Asn Phe Val Leu Gly Glu Asp Cys Trp Val
        195                 200                 205

Ala Gly Gly Val Met Arg Asp Met Glu Asn Pro Ser Arg Gly Gly Gln
    210                 215                 220

Pro Ala His Met Lys Asp Tyr Lys Tyr Lys Thr Met Asn Asp Asp Asn
225                 230                 235                 240

Gly Gly Val His Thr Asn Ser Gly Ile Ile Asn His Ala Ala Tyr Leu
                245                 250                 255

Val Ala Asp Gly Ile Glu Lys Thr Gly Ala Lys Asn Ser Lys Asp Ile
            260                 265                 270

Met Gly Lys Ile Phe Tyr Thr Ala Asn Cys Tyr Lys Trp Asp Glu Thr
        275                 280                 285

Thr Asn Phe Ala Lys Cys Arg Asn Asp Val Val Gln Val Thr Lys Glu
    290                 295                 300

Leu Tyr Gly Glu Asn Ser Asn Tyr Val Lys Ile Val Glu Lys Ala Phe
305                 310                 315                 320

Asp Gln Val Gly Ile Thr Ala Thr Pro Gln Leu Pro Leu
                325                 330

<210> SEQ ID NO 2
<211> LENGTH: 581
<212> TYPE: PRT
<213> ORGANISM: Clostridium Botulinum

<400> SEQUENCE: 2

Met Lys Ser Lys Lys Leu Leu Ala Thr Val Leu Ser Ala Val Ile Thr
1               5                   10                  15

Phe Ser Thr Val Ser Ala Val Tyr Ala Ala Pro Val Gly Lys Glu Ser
            20                  25                  30

Lys Val Glu Pro Lys Thr Thr Thr Ile Thr Trp Glu Lys Asn Glu Gln
        35                  40                  45

Asn Thr Lys Lys Ala Ala Thr Asp Ile Thr Glu Lys Lys Phe Asn Asn
    50                  55                  60

Ser Glu Glu Ile Thr Lys Phe Phe Glu Lys Asn Ile Ser Lys Phe Gly
65                  70                  75                  80

Val Gln Lys Gly Ser Leu Lys Asn Thr Lys Thr Val Lys Asp Glu Lys
                85                  90                  95

Gly Lys Thr Asn Tyr His Met Ile Tyr Glu Val Glu Gly Ile Pro Val
            100                 105                 110

Tyr Tyr Gly Arg Ile Val Phe Thr Thr Glu Lys Asp Ser Ser Met Asp
        115                 120                 125

Ser Ile Asn Gly Arg Ile Asp Thr Val Phe Glu Asn Gly Asn Trp Lys
    130                 135                 140

Asn Lys Ile Lys Leu Ser Lys Glu Asp Ala Ile Ala Lys Ala Lys Asn
145                 150                 155                 160

Asp Ile Lys Asp Glu Lys Ala Thr Ser Lys Lys Thr Asp Leu Tyr Leu
```

-continued

```
                165                 170                 175
Tyr Asn Phe Glu Gly Lys Pro Tyr Val Val Tyr Leu Val Asp Leu Ile
            180                 185                 190
Thr Asp Asn Gly Ser Trp Thr Val Phe Val Asn Ala Glu Asp Gly Ser
        195                 200                 205
Ile Val Asn Lys Phe Asn Asn Thr Pro Thr Leu Ile Asp Thr Lys Asp
    210                 215                 220
Gln Lys Leu Pro Asn Ala Lys Lys Ile Lys Asp Glu Ala Lys Lys Ala
225                 230                 235                 240
Ser Asn Ala Asn Asn Val Ile Asp Val Gln Gly Gln Ser Val Lys Gly
                245                 250                 255
Val Gly Lys Thr Ser Leu Asp Gly Leu Val Asn Ile Asp Val Thr Tyr
            260                 265                 270
Gly Asn Gly Lys Tyr Tyr Leu Lys Asp Ser Asn Lys Asn Ile Tyr Leu
        275                 280                 285
Tyr Asp Leu Lys Asn Gln Val Asp Glu Tyr Asp Leu Tyr Asn Tyr Leu
    290                 295                 300
Ser Arg Pro Asn Tyr Lys Gln Ile Leu Met Ser Lys Ser Glu Leu Ile
305                 310                 315                 320
Ser Asn Tyr Asn Asn Asn Phe Ile Ala Asn Asn Gln Val Asn Ser Val
                325                 330                 335
Asp Ala Tyr Val Asn Thr Asn Lys Thr Tyr Asp Tyr Tyr Lys Asn Lys
            340                 345                 350
Leu Asn Arg Asn Ser Ile Asp Asn Lys Gly Met Asn Ile Asn Gly Phe
        355                 360                 365
Val His Val Gly Arg Asn Tyr Gly Asn Ala Phe Trp Tyr Gly Pro Tyr
    370                 375                 380
Asp Gly Met Phe Phe Gly Asp Gly Asp Gly Ile Tyr Phe Ser Ser Leu
385                 390                 395                 400
Ala Lys Ser Leu Asp Val Val Gly His Glu Leu Ser His Gly Val Thr
                405                 410                 415
Asn Lys Glu Ser Asn Leu Lys Tyr Glu Asn Glu Ser Gly Ala Leu Asn
            420                 425                 430
Glu Ser Phe Ser Asp Ile Met Gly Val Ala Val Glu Gly Lys Asn Phe
        435                 440                 445
Val Leu Gly Glu Asp Cys Trp Val Ala Gly Gly Val Met Arg Asp Met
    450                 455                 460
Glu Asn Pro Ser Arg Gly Gly Gln Pro Ala His Met Lys Asp Tyr Lys
465                 470                 475                 480
Tyr Lys Thr Met Asn Asp Asp Asn Gly Gly Val His Thr Asn Ser Gly
                485                 490                 495
Ile Ile Asn His Ala Ala Tyr Leu Val Ala Asp Gly Ile Glu Lys Thr
            500                 505                 510
Gly Ala Lys Asn Ser Lys Asp Ile Met Gly Lys Ile Phe Tyr Thr Ala
        515                 520                 525
Asn Cys Tyr Lys Trp Asp Glu Thr Thr Asn Phe Ala Lys Cys Arg Asn
    530                 535                 540
Asp Val Val Gln Val Thr Lys Glu Leu Tyr Gly Glu Asn Ser Asn Tyr
545                 550                 555                 560
Val Lys Ile Val Glu Lys Ala Phe Asp Gln Val Gly Ile Thr Ala Thr
                565                 570                 575
Pro Gln Leu Pro Leu
            580
```

<210> SEQ ID NO 3
<211> LENGTH: 1296
<212> TYPE: PRT
<213> ORGANISM: Clostridium Botulinum

<400> SEQUENCE: 3

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
```

```
            370                 375                 380
Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800
```

-continued

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
            885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
            965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg
            1010                1015                1020

Leu Asn Asn Ser Lys Ile Tyr Ile Asn Gly Arg Leu Ile Asp Gln
            1025                1030                1035

Lys Pro Ile Ser Asn Leu Gly Asn Ile His Ala Ser Asn Asn Ile
            1040                1045                1050

Met Phe Lys Leu Asp Gly Cys Arg Asp Thr His Arg Tyr Ile Trp
            1055                1060                1065

Ile Lys Tyr Phe Asn Leu Phe Asp Lys Glu Leu Asn Glu Lys Glu
            1070                1075                1080

Ile Lys Asp Leu Tyr Asp Asn Gln Ser Asn Ser Gly Ile Leu Lys
            1085                1090                1095

Asp Phe Trp Gly Asp Tyr Leu Gln Tyr Asp Lys Pro Tyr Tyr Met
            1100                1105                1110

Leu Asn Leu Tyr Asp Pro Asn Lys Tyr Val Asp Val Asn Asn Val
            1115                1120                1125

Gly Ile Arg Gly Tyr Met Tyr Leu Lys Gly Pro Arg Gly Ser Val
            1130                1135                1140

Met Thr Thr Asn Ile Tyr Leu Asn Ser Ser Leu Tyr Arg Gly Thr
            1145                1150                1155

Lys Phe Ile Ile Lys Lys Tyr Ala Ser Gly Asn Lys Asp Asn Ile
            1160                1165                1170

Val Arg Asn Asn Asp Arg Val Tyr Ile Asn Val Val Val Lys Asn
            1175                1180                1185

Lys Glu Tyr Arg Leu Ala Thr Asn Ala Ser Gln Ala Gly Val Glu
            1190                1195                1200

-continued

```
Lys Ile Leu Ser Ala Leu Glu Ile Pro Asp Val Gly Asn Leu Ser
    1205                1210                1215

Gln Val Val Val Met Lys Ser Lys Asn Asp Gln Gly Ile Thr Asn
    1220                1225                1230

Lys Cys Lys Met Asn Leu Gln Asp Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295

<210> SEQ ID NO 4
<211> LENGTH: 25
<212> TYPE: PRT
<213> ORGANISM: Clostridium Botulinum
<220> FEATURE:
<221> NAME/KEY: Loop BoNT/A1
<222> LOCATION: (1)..(25)

<400> SEQUENCE: 4

Cys Val Arg Gly Ile Ile Thr Ser Lys Thr Lys Ser Leu Asp Lys Gly
1               5                   10                  15

Tyr Asn Lys Ala Leu Asn Asp Leu Cys
            20                  25

<210> SEQ ID NO 5
<211> LENGTH: 25
<212> TYPE: PRT
<213> ORGANISM: Clostridium Botulinum
<220> FEATURE:
<221> NAME/KEY: Loop BoNT/A2/A6
<222> LOCATION: (1)..(25)

<400> SEQUENCE: 5

Cys Val Arg Gly Ile Ile Pro Phe Lys Thr Lys Ser Leu Asp Glu Gly
1               5                   10                  15

Tyr Asn Lys Ala Leu Asn Asp Leu Cys
            20                  25

<210> SEQ ID NO 6
<211> LENGTH: 25
<212> TYPE: PRT
<213> ORGANISM: Clostridium Botulinum
<220> FEATURE:
<221> NAME/KEY: Loop BoNT/A3
<222> LOCATION: (1)..(25)

<400> SEQUENCE: 6

Cys Val Arg Gly Ile Ile Pro Phe Lys Thr Lys Ser Leu Asp Glu Gly
1               5                   10                  15

Tyr Asn Lys Ala Leu Asn Asp Leu Cys
            20                  25

<210> SEQ ID NO 7
<211> LENGTH: 25
<212> TYPE: PRT
<213> ORGANISM: Clostridium Botulinum
<220> FEATURE:
<221> NAME/KEY: Loop BoNT/A3
```

```
<222> LOCATION: (1)..(25)

<400> SEQUENCE: 7

Cys Val Arg Gly Ile Ile Pro Phe Lys Thr Lys Ser Leu Asp Glu Gly
1               5                   10                  15

Tyr Asn Lys Ala Leu Asn Tyr Leu Cys
            20                  25

<210> SEQ ID NO 8
<211> LENGTH: 25
<212> TYPE: PRT
<213> ORGANISM: Clostridium Botulinum
<220> FEATURE:
<221> NAME/KEY: Loop BoNT/A4
<222> LOCATION: (1)..(25)

<400> SEQUENCE: 8

Cys Val Arg Gly Ile Ile Thr Ser Lys Thr Lys Ser Leu Asp Glu Gly
1               5                   10                  15

Tyr Asn Lys Ala Leu Asn Glu Leu Cys
            20                  25

<210> SEQ ID NO 9
<211> LENGTH: 25
<212> TYPE: PRT
<213> ORGANISM: Clostridium Botulinum
<220> FEATURE:
<221> NAME/KEY: Loop BoNT/A5
<222> LOCATION: (1)..(25)

<400> SEQUENCE: 9

Cys Val Arg Gly Ile Ile Thr Ser Lys Thr Lys Ser Leu Asp Glu Gly
1               5                   10                  15

Tyr Asn Lys Ala Leu Asn Asp Leu Cys
            20                  25

<210> SEQ ID NO 10
<211> LENGTH: 25
<212> TYPE: PRT
<213> ORGANISM: Clostridium Botulinum
<220> FEATURE:
<221> NAME/KEY: Loop BoNT/A7
<222> LOCATION: (1)..(25)

<400> SEQUENCE: 10

Trp Val Arg Gly Ile Ile Pro Phe Lys Pro Lys Ser Leu Asp Glu Gly
1               5                   10                  15

Ser Asn Lys Ala Leu Asn Asp Leu Cys
            20                  25

<210> SEQ ID NO 11
<211> LENGTH: 10
<212> TYPE: PRT
<213> ORGANISM: Clostridium Botulinum
<220> FEATURE:
<221> NAME/KEY: Loop BoNT/B1/B4bv/B6
<222> LOCATION: (1)..(10)

<400> SEQUENCE: 11

Cys Lys Ser Val Lys Ala Pro Gly Ile Cys
1               5                   10

<210> SEQ ID NO 12
<211> LENGTH: 10
<212> TYPE: PRT
```

<213> ORGANISM: Clostridium Botulinum
<220> FEATURE:
<221> NAME/KEY: Loop BoNT/B2/B3
<222> LOCATION: (1)..(10)

<400> SEQUENCE: 12

Cys Lys Ser Val Arg Ala Pro Gly Ile Cys
1               5                   10

<210> SEQ ID NO 13
<211> LENGTH: 10
<212> TYPE: PRT
<213> ORGANISM: Clostridium Botulinum
<220> FEATURE:
<221> NAME/KEY: Loop BoNT/B5np
<222> LOCATION: (1)..(10)

<400> SEQUENCE: 13

Cys Lys Ser Val Lys Val Pro Gly Ile Cys
1               5                   10

<210> SEQ ID NO 14
<211> LENGTH: 17
<212> TYPE: PRT
<213> ORGANISM: Clostridium Botulinum
<220> FEATURE:
<221> NAME/KEY: Loop BoNT/C/CD
<222> LOCATION: (1)..(17)

<400> SEQUENCE: 14

Cys His Lys Ala Ile Asp Gly Arg Ser Leu Tyr Asn Lys Thr Leu Asp
1               5                   10                  15

Cys

<210> SEQ ID NO 15
<211> LENGTH: 14
<212> TYPE: PRT
<213> ORGANISM: Clostridium Botulinum
<220> FEATURE:
<221> NAME/KEY: Loop BoNT/D
<222> LOCATION: (1)..(14)

<400> SEQUENCE: 15

Cys Leu Arg Leu Thr Lys Asn Ser Arg Asp Asp Ser Thr Cys
1               5                   10

<210> SEQ ID NO 16
<211> LENGTH: 14
<212> TYPE: PRT
<213> ORGANISM: Clostridium Botulinum
<220> FEATURE:
<221> NAME/KEY: Loop BoNT/DC
<222> LOCATION: (1)..(14)

<400> SEQUENCE: 16

Cys Leu Arg Leu Thr Arg Asn Ser Arg Asp Asp Ser Thr Cys
1               5                   10

<210> SEQ ID NO 17
<211> LENGTH: 15
<212> TYPE: PRT
<213> ORGANISM: Clostridium Botulinum
<220> FEATURE:
<221> NAME/KEY: Loop BoNT/E1-E5
<222> LOCATION: (1)..(15)

<400> SEQUENCE: 17

Cys Lys Asn Ile Val Ser Val Lys Gly Ile Arg Lys Ser Ile Cys
1               5                   10                  15

<210> SEQ ID NO 18
<211> LENGTH: 15
<212> TYPE: PRT
<213> ORGANISM: Clostridium Botulinum
<220> FEATURE:
<221> NAME/KEY: Loop BoNT/E6
<222> LOCATION: (1)..(15)

<400> SEQUENCE: 18

Cys Lys Asn Ile Val Phe Ser Lys Gly Ile Arg Lys Ser Ile Cys
1               5                   10                  15

<210> SEQ ID NO 19
<211> LENGTH: 17
<212> TYPE: PRT
<213> ORGANISM: Clostridium Botulinum
<220> FEATURE:
<221> NAME/KEY: Loop BoNT/F1/F6
<222> LOCATION: (1)..(17)

<400> SEQUENCE: 19

Cys Lys Ser Val Ile Pro Arg Lys Gly Thr Lys Ala Pro Pro Arg Leu
1               5                   10                  15

Cys

<210> SEQ ID NO 20
<211> LENGTH: 17
<212> TYPE: PRT
<213> ORGANISM: Clostridium Botulinum
<220> FEATURE:
<221> NAME/KEY: Loop BoNT/F2/F3
<222> LOCATION: (1)..(17)

<400> SEQUENCE: 20

Cys Lys Ser Ile Ile Pro Arg Lys Gly Thr Lys Gln Ser Pro Ser Leu
1               5                   10                  15

Cys

<210> SEQ ID NO 21
<211> LENGTH: 17
<212> TYPE: PRT
<213> ORGANISM: Clostridium Botulinum
<220> FEATURE:
<221> NAME/KEY: Loop BoNT/F4
<222> LOCATION: (1)..(17)

<400> SEQUENCE: 21

Cys Lys Ser Ile Ile Pro Arg Lys Gly Thr Lys Ala Pro Pro Arg Leu
1               5                   10                  15

Cys

<210> SEQ ID NO 22
<211> LENGTH: 15
<212> TYPE: PRT
<213> ORGANISM: Clostridium Botulinum
<220> FEATURE:
<221> NAME/KEY: Loop BoNT/F5
<222> LOCATION: (1)..(15)

<400> SEQUENCE: 22

Cys Leu Asn Ser Ser Phe Lys Lys Asn Thr Lys Lys Pro Leu Cys
1               5                   10                  15

<210> SEQ ID NO 23
<211> LENGTH: 15
<212> TYPE: PRT
<213> ORGANISM: Clostridium Botulinum
<220> FEATURE:
<221> NAME/KEY: Loop BoNT/F7
<222> LOCATION: (1)..(15)

<400> SEQUENCE: 23

Cys Lys Ser Ile Val Ser Lys Lys Gly Thr Lys Asn Ser Leu Cys
1               5                   10                  15

<210> SEQ ID NO 24
<211> LENGTH: 15
<212> TYPE: PRT
<213> ORGANISM: Clostridium Botulinum
<220> FEATURE:
<221> NAME/KEY: Loop BoNT/G
<222> LOCATION: (1)..(15)

<400> SEQUENCE: 24

Cys Lys Pro Val Met Tyr Lys Asn Thr Gly Lys Ser Glu Gln Cys
1               5                   10                  15

<210> SEQ ID NO 25
<211> LENGTH: 29
<212> TYPE: PRT
<213> ORGANISM: Clostridium Tetani
<220> FEATURE:
<221> NAME/KEY: Loop TeNT
<222> LOCATION: (1)..(29)

<400> SEQUENCE: 25

Cys Lys Lys Ile Ile Pro Pro Thr Asn Ile Arg Glu Asn Leu Tyr Asn
1               5                   10                  15

Arg Thr Ala Ser Leu Thr Asp Leu Gly Gly Glu Leu Cys
            20                  25

<210> SEQ ID NO 26
<211> LENGTH: 1005
<212> TYPE: DNA
<213> ORGANISM: C. Botulinum

<400> SEQUENCE: 26
atggttcaag gtcaaagcgt taaggagta ggaaaaacta gcttggatgg actagtaaat        60
attgatgtaa cttatggaaa tggaaaatac tatttaaaag atagcaacaa aaatatttat      120
ctatatgact aaaaaatca agttgatgaa tatgatctat acaattatct tagtagacct       180
aactataaac aaatattaat gagcaaatct gaattaatat ctaattacaa taataatttt      240
atagccaaca atcaggttaa ttctgtagat gcttatgtaa acacaaataa aacctatgat      300
tattataaaa acaaattaaa tagaaacagt attgataata agggtatgaa tattaatggg      360
tttgttcatg taggtagaaa ttatggtaat gcttttttggt acggtccata tgatgggatg     420
ttctttggcg atggcgacgg aatatacttc tcttcccttg caaatctttt agatgttgta      480
ggccacgaat taagtcatgg tgtaacaaat aaagagtcta atcttaaata tgaaaatgaa      540
tctggtgccc taaatgaatc tttctcagat attatgggag tagctgttga gggtaaaaac      600
tttgtactag gtgaagattg ctgggttgct ggaggagtaa tgagagatat ggaaaatcca      660
tccagaggag ccaaccagc tcatatgaaa gattataaat acaaaactat gaatgacgat       720
aacggtggtg ttcatacaaa ttcaggtata ataaaccatg ctgcttattt agttgcagat      780

```
ggaatagaaa aaactggtgc aaaaaatagt aaagatatta tgggaaaaat attctataca    840
gctaattgct ataaatggga tgaaacaaca aattttgcta agtgcagaaa tgatgtagtc    900
caagttacta aagaacttta tggcgaaaat agcaactatg taaaaattgt tgaaaaagct    960
tttgaccaag ttggaataac tgctacacct caattaccat ataa                    1005

<210> SEQ ID NO 27
<211> LENGTH: 1746
<212> TYPE: DNA
<213> ORGANISM: Clostridium Botulinum

<400> SEQUENCE: 27
atgaaaagta aaaattatt agctacagtg ctaagtgccg tgatcacttt ttctactgtt     60
tctgcagttt atgctgcgcc tgtaggaaaa gaaagtaaag ttgaaccaaa actacaaca   120
ataacttggg aaaaaaatga acaaaatact aaaaaagctg ctactgatat aactgaaaag   180
aaatttaaca attctgagga gataactaaa ttctttgaaa aaatatatc taaatttggt   240
gtacaaaaag gttctcttaa aaacaccaag actgtaaaag acgaaaaagg taaaactaac   300
tatcatatga tttatgaagt agaaggtata cctgtatact atggaagaat tgtttttaca   360
actgaaaaag actcctccat ggattctata acggtagaa ttgatactgt ttttgaaaat    420
gggaattgga aaacaaaat caaactatca aaagaagatg ctatagcaaa agctaaaaat   480
gatattaaag atgaaaaagc aactagtaaa aagaccgatt tatatctgta aattttgag    540
ggcaaaacctt atgtagttta tttagtagat ctaattacag acaacgggag ttggacggtt   600
ttcgttaatg ctgaggatgg ttctatagta aataaattta ataatactcc tactttaatt    660
gatactaaag atcaaaaatt acccaatgct aaaaaaatta agatgaagc taaaaaagct    720
agtaatgcaa ataatgtaat tgatgttcaa ggtcaaagcg ttaaaggagt aggaaaaact   780
agcttggatg gactagtaaa tattgatgta acttatggaa atggaaaata ctatttaaaa    840
gatagcaaca aaaatattta tctatatgac ttaaaaaatc aagttgatga atatgatcta    900
tacaattatc ttagtagacc taactataaa caaatattaa tgagcaaatc tgaattaata    960
tctaattaca ataataattt tatagccaac aatcaggtta attctgtaga tgcttatgta   1020
aacacaaata aaacctatga ttattataaa acaaattaa atagaaacag tattgataat   1080
aagggtatga atattaatgg gtttgttcat gtaggtagaa attatggtaa tgcttttttgg   1140
tacggtccat atgatgggat gttctttggc gatggcgacg gaatatactt ctcttcccttt   1200
gcaaaatctt tagatgttgt aggccacgaa ttaagtcatg gtgtaacaaa taagagtct    1260
aatcttaaat atgaaaatga atctggtgcc ctaaatgaat cttttctcaga tattatggga   1320
gtagctgttg agggtaaaaa ctttgtacta ggtgaagatt gctgggttgc tggaggagta   1380
atgagagata tggaaaatcc atccagagga ggccaaccag ctcatatgaa agattataaa   1440
tacaaaacta tgaatgacga taacggtggt gttcatacaa attcaggtat aataaaccat   1500
gctgcttatt tagttgcaga tggaatagaa aaactggtg caaaaaatag taagagatat    1560
atgggaaaaa tattctatac agctaattgc tataaatggg atgaaacaac aaattttgct   1620
aagtgcagaa atgatgtagt ccaagttact aaagaacttt atggcgaaaa tagcaactat   1680
gtaaaaattg ttgaaaaagc ttttgaccaa gttggaataa ctgctacacc tcaattacca   1740
ttataa                                                              1746
```